United States Patent
von Schenck et al.

(10) Patent No.: US 12,239,600 B2
(45) Date of Patent: *Mar. 4, 2025

(54) CPR CHEST COMPRESSION SYSTEM PERIODICALLY REMINDING ATTENDANT TO CHECK PATIENT

(71) Applicants: STRYKER CORPORATION, Kalamazoo, MI (US); JOLIFE AB, Lund (SE); PHYSIO-CONTROL, INC., Remond, WA (US)

(72) Inventors: Erik von Schenck, Lomma (SE); Anders Nilsson, Akarp (SE); Sara Lindroth, Lund (SE); Robert Walker, Seattle, WA (US); Fred Chapman, Newcastle, WA (US); Krystyna Szul, Seattle, WA (US); Gregory T. Kavounas, Bellevue, WA (US)

(73) Assignees: STRYKER CORPORATION, Portage, MI (US); JOLIFE AB, Lund (SE); PHYSIO-CONTROL, INC., Redmond, WA (US)

( * ) Notice: Subject to any disclaimer, the term of this patent is extended or adjusted under 35 U.S.C. 154(b) by 858 days.

This patent is subject to a terminal disclaimer.

(21) Appl. No.: 17/026,701

(22) Filed: Sep. 21, 2020

(65) Prior Publication Data
US 2021/0000684 A1   Jan. 7, 2021

Related U.S. Application Data

(63) Continuation of application No. 15/616,698, filed on Jun. 7, 2017, now Pat. No. 10,835,450.
(Continued)

(51) Int. Cl.
*A61H 31/00*    (2006.01)
*A61B 5/00*     (2006.01)
*A61B 5/318*    (2021.01)

(52) U.S. Cl.
CPC ......... *A61H 31/006* (2013.01); *A61H 31/005* (2013.01); *A61H 31/008* (2013.01);
(Continued)

(58) Field of Classification Search
CPC .. A61H 31/006; A61H 31/005; A61H 31/004; A61H 31/008; A61H 2031/001;
(Continued)

(56) References Cited

U.S. PATENT DOCUMENTS

| | | |
|---|---|---|
| 4,326,507 A | 4/1982 | Barkalow |
| 4,451,158 A | 5/1984 | Selwyn et al. |

(Continued)

FOREIGN PATENT DOCUMENTS

| | | |
|---|---|---|
| WO | 0027334 A2 | 5/2000 |
| WO | 2006039166 A1 | 4/2006 |

(Continued)

OTHER PUBLICATIONS

American Heart Association, Highlights of the 2015 American Heart Association Guidelines Update for CPR and ECC, 2015 (Year: 2015).
(Continued)

*Primary Examiner* — Joseph D. Boecker
*Assistant Examiner* — Brian T Khong
(74) *Attorney, Agent, or Firm* — Miller Nash LLP

(57) ABSTRACT

In embodiments, a CPR chest compression system includes a retention structure that can retain the patient's body, and a compression mechanism that can perform automatically CPR compressions and releases to the patient's chest. The compression mechanism can pause the performing of the CPR compressions for a short time, so that an attendant can check the patient. The CPR system also includes a user interface that can output a human-perceptible check patient prompt, to alert an attendant to check the patient during the (Continued)

METHODS pause. An advantage can be when the attendant checks in situations where the condition of the patient might have changed, and an adjustment is needed. Or in situations where the patient may have improved enough to where the compressions are no longer needed.

18 Claims, 16 Drawing Sheets

Related U.S. Application Data

(60) Provisional application No. 62/441,096, filed on Dec. 30, 2016.

(52) U.S. Cl.
CPC ............. *A61B 5/318* (2021.01); *A61B 5/4848* (2013.01); *A61B 2505/01* (2013.01); *A61H 2201/0119* (2013.01); *A61H 2201/1246* (2013.01); *A61H 2201/5007* (2013.01); *A61H 2201/5046* (2013.01); *A61H 2201/5058* (2013.01); *A61H 2201/5061* (2013.01); *A61H 2230/206* (2013.01); *A61H 2230/208* (2013.01); *A61H 2230/305* (2013.01); *A61H 2230/655* (2013.01)

(58) Field of Classification Search
CPC ........ A61H 2031/002; A61H 2031/003; A61B 2505/01; A61B 2505/03
See application file for complete search history.

(56) References Cited

U.S. PATENT DOCUMENTS

| | | | |
|---|---|---|---|
| 4,583,524 A | 4/1986 | Hutchins | |
| 4,863,385 A | 9/1989 | Pierce | |
| 5,261,394 A | 11/1993 | Mulligan et al. | |
| 5,394,892 A * | 3/1995 | Kenny | A61H 31/005 601/41 |
| 5,496,257 A | 3/1996 | Kelly | |
| 5,640,078 A | 6/1997 | Kou et al. | |
| 5,741,305 A | 4/1998 | Vincent et al. | |
| 6,066,106 A | 5/2000 | Sherman et al. | |
| 6,090,056 A | 7/2000 | Bystrom | |
| 6,601,583 B2 | 8/2003 | Pessala et al. | |
| 6,939,315 B2 | 9/2005 | Sherman et al. | |
| 7,308,304 B2 | 12/2007 | Hampton et al. | |
| 7,569,021 B2 | 8/2009 | Sebelius et al. | |
| 9,198,826 B2 | 12/2015 | Banville et al. | |
| 9,713,568 B2 | 7/2017 | Nilsson et al. | |
| 2002/0177793 A1 | 11/2002 | Sherman et al. | |
| 2004/0082888 A1 | 4/2004 | Palazzolo et al. | |
| 2004/0215244 A1 | 10/2004 | Marcovecchio et al. | |
| 2005/0131465 A1 | 6/2005 | Freeman et al. | |
| 2006/0094991 A1 | 5/2006 | Walker | |
| 2006/0155222 A1 | 7/2006 | Sherman et al. | |
| 2006/0173499 A1 | 8/2006 | Hampton et al. | |
| 2006/0229680 A1 * | 10/2006 | Chapman | A61N 1/39044 607/5 |
| 2007/0093731 A1 | 4/2007 | Warwick et al. | |
| 2012/0016279 A1 * | 1/2012 | Banville | A61B 5/318 601/41 |
| 2012/0116272 A1 | 5/2012 | Hampton et al. | |
| 2012/0203147 A1 | 8/2012 | Lurie et al. | |
| 2012/0330199 A1 | 12/2012 | Lurie et al. | |
| 2012/0330200 A1 * | 12/2012 | Voss | A61H 31/004 601/41 |
| 2013/0218056 A1 | 8/2013 | Aelen et al. | |
| 2013/0296727 A1 | 11/2013 | Sullivan et al. | |
| 2013/0324894 A1 | 12/2013 | Herken et al. | |
| 2014/0039359 A1 | 2/2014 | Madanat | |
| 2014/0046228 A1 * | 2/2014 | Walker | A61H 31/008 601/41 |
| 2014/0088467 A1 | 3/2014 | Parascandola et al. | |
| 2014/0094724 A1 | 4/2014 | Freeman | |
| 2014/0107541 A1 * | 4/2014 | Sullivan | A61H 31/006 601/41 |
| 2014/0236053 A1 | 8/2014 | Walker et al. | |
| 2014/0303530 A1 * | 10/2014 | Nilsson | A61H 31/005 601/41 |
| 2014/0336546 A1 | 11/2014 | Chapman et al. | |
| 2014/0358048 A1 | 12/2014 | Sullivan et al. | |
| 2015/0231028 A1 | 8/2015 | Belalcazar | |
| 2015/0313493 A1 | 11/2015 | Sullivan | |
| 2015/0352002 A1 | 12/2015 | Jeppsson et al. | |
| 2016/0067140 A1 | 3/2016 | Banville et al. | |
| 2016/0136042 A1 * | 5/2016 | Nilsson | A61H 31/006 601/41 |
| 2016/0143804 A1 | 5/2016 | Nilsson et al. | |
| 2016/0157739 A1 | 6/2016 | Peeters et al. | |
| 2016/0213560 A1 * | 7/2016 | Sturdivant | A61N 1/39044 |
| 2016/0296419 A1 * | 10/2016 | Paulussen | A61H 31/006 |
| 2016/0317384 A1 | 11/2016 | Silver et al. | |
| 2017/0000688 A1 | 1/2017 | Kaufman et al. | |
| 2017/0021182 A1 | 1/2017 | Fossan | |
| 2017/0119622 A1 | 5/2017 | Lurie et al. | |
| 2019/0053975 A1 | 2/2019 | Schenck et al. | |

FOREIGN PATENT DOCUMENTS

| | | |
|---|---|---|
| WO | 2006039166 A2 | 4/2006 |
| WO | 2014051934 A1 | 4/2014 |
| WO | 2016097938 A1 | 6/2016 |

OTHER PUBLICATIONS

Callahan, Thomas; Letter regarding approval of marketing Thumper® Model 1007, 1997, pp. 6-7 of 307 & pp. 194-195 of 307, Food and Drug Administration, Rockville, MD.

International Search Report and Written Opinion issued in PCT/US2017/068348, dated May 2, 2018. 32 pages.

Extended European Search Report issued in European Patent Application No. 17886013.6, dated Dec. 7, 2020, 8 pages.

* cited by examiner

FIG. 13  *METHODS*

FIG. 23          METHODS

CPR CHEST COMPRESSION SYSTEM PERIODICALLY REMINDING ATTENDANT TO CHECK PATIENT

CROSS REFERENCE TO RELATED PATENT APPLICATIONS

This patent application is a continuation of U.S. patent application Ser. No. 15/616,698, filed on Jun. 7, 2017, which claims priority from U.S. Provisional Patent Application Ser. No. 62/441,096, filed on Dec. 30, 2016, the disclosures of which, as initially made, are hereby incorporated by reference.

BACKGROUND

In certain types of medical emergencies a patient's heart stops working, which stops the blood from flowing. Without the blood flowing, organs like the brain will start becoming damaged, and the patient will soon die. Cardiopulmonary resuscitation (CPR) can forestall these risks. CPR includes performing repeated chest compressions to the chest of the patient, so as to cause the patient's blood to circulate some. CPR also includes delivering rescue breaths to the patient, so as to create air circulation in the lungs.

CPR is intended to merely forestall organ damage and death, until a more definitive treatment is made available. Defibrillation is one such definitive treatment: it is an electric shock delivered deliberately to the patient's heart, in the hope of restoring the heart rhythm.

Traditionally, CPR has been performed manually. A number of people have been trained in CPR, including some who are not in the medical professions, just in case they are bystanders in a medical emergency event.

Guidelines by medical experts such as the American Heart Association provide parameters for CPR to cause the blood to circulate effectively. The parameters are for aspects such as the frequency of the chest compressions, the depth that they should reach, and the full release that is to follow each of them. If the patient is an adult, the depth is sometimes required to reach or exceed 5 cm (2 in.). The parameters for CPR may also include instructions for the rescue breaths.

International guidelines for performing cardiopulmonary resuscitation (CPR) recommend chest compressions that are consistent and repetitive in duty cycle, depth, and rate, among other characteristics. Furthermore, recommendations for hand placement during CPR are not more specific than pushing in the center of the chest at the sternum. This is, presumably, to press on the heart, or "pump," that generates blood flow.

The repeated chest compressions of CPR are actually compressions alternating with releases. The compressions cause the chest to be compressed from its original shape. During the releases the chest is decompressing, which means that the chest is undergoing the process of returning to its original shape. This decompressing does not happen immediately upon a quick release. In fact, full decompression might not be attained by the time the next compression is performed.

Manual CPR may be ineffective, however. Indeed, the rescuer might not be able to recall their training, especially under the stress of the moment. And even the best trained rescuer can become fatigued from performing chest compressions for a long time, at which point their performance may become degraded. In the end, chest compressions that are not frequent enough, not deep enough, or not followed by full releases may fail to maintain the blood circulation required to forestall organ damage and death.

The risk of ineffective chest compressions has been addressed with CPR chest compression machines. Such machines have been known by a number of names, for example CPR chest compression machines, CPR machines, mechanical CPR devices, cardiac compressors, CPR devices, CPR systems, and so on.

CPR chest compression machines typically hold the patient supine, which means lying on his or her back. Such machines then repeatedly compress and release the chest of the patient. In fact, they can be programmed to automatically follow the guidelines, by compressing and releasing at the recommended rate or frequency, while reaching a specific depth.

Another challenge is that the chest may start collapsing due to the repeated compressions, which means that it might not fully return to its original height, even if it were given ample opportunity to do so. In such instances, the lungs might not be able to receive enough air without the rescue breaths of a ventilator.

Some CPR chest compression machines compress the chest by a piston. Some may even have a suction cup at the end of the piston, with which these machines lift the chest at least during the releases. This lifting may actively assist the chest, in decompressing the chest faster than the chest would accomplish by itself. This type of lifting is sometimes called active decompression, and may improve air circulation in the patient, especially when the chest could be collapsing due to the repeated compressions.

Some CPR chest compression machines work so reliably that the rescuer tending to the patient may neglect to occasionally check the patient. Rescuers at an emergency scene may be understandably preoccupied with other tasks, and not notice that the patient needs additional attention, or that a condition of the patient may have changed.

BRIEF SUMMARY

The present description gives instances of CPR chest compression systems, storage media that store programs and methods, the use of which may help overcome problems and limitations of the prior art.

In embodiments, a CPR chest compression system includes a retention structure that can retain the patient's body, and a compression mechanism that can perform automatically CPR compressions to the patient's chest, alternating with releases of the CPR compressions. The compression mechanism can pause the performing of the CPR compressions for a short time, so that an attendant can check the patient. The CPR system also includes a user interface that can output a human-perceptible check patient prompt, to alert the attendant to check the patient during the pause. An advantage can be when the attendant checks in situations where the condition of the patient might have changed, and an adjustment is needed. Or in situations where the patient may have improved enough to where the compressions are no longer needed.

In embodiments, a CPR chest compression system is capable of operation that can be paused temporarily by a rescuer. Such a CPR system may include a retention structure that can retain the patient's body, and a compression mechanism that can perform automatically CPR compressions to the patient's chest, alternating with releases of the CPR compressions. The CPR system may also include a user interface with a pause means that the rescuer can actuate. When the rescuer does this, the compression mechanism can pause the performing of the CPR compressions for a short time, so that the attendant can check the patient. An advantage can be when the attendant checks in situations where the condition of the patient might have changed, and an adjustment is needed. Or in situations where the patient may have improved enough to where the compressions are no longer needed.

In embodiments, a CPR chest compression system can warn the rescuer upon restarting from a pause. Such a CPR system may include a retention structure that can retain the patient's body, and a compression mechanism that can perform automatically CPR compressions to the patient's chest, alternating with releases of the CPR compressions. The compression mechanism can pause the performing of the CPR compressions for a short time, so that the attendant can check the patient. The CPR system may also include a user interface with an output device that outputs a human-perceptible restart warning to the rescuer, in connection with the end of the pause time duration. An advantage can be that the rescuer can handle the patient more safely.

These and other features and advantages of the claimed invention will become more readily apparent in view of the embodiments described and illustrated in the present disclosure, namely from the present written specification and the drawings.

DETAILED DESCRIPTION

Figure 1:
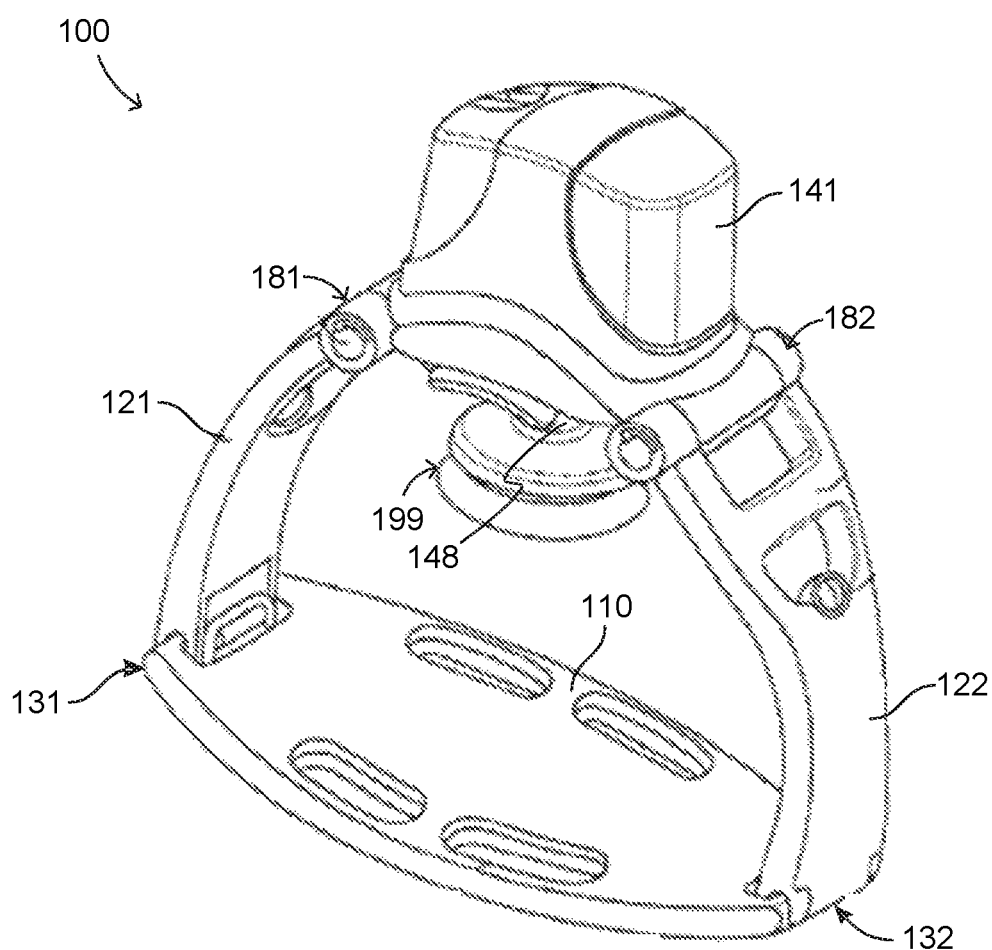
FIG. 1 is a perspective diagram of a conventional CPR system.

As has been mentioned, the present description is about Cardio-Pulmonary Resuscitation (CPR) systems that are usable by a rescuer to care for a patient, and related processors and methods. A conventional such system is now described with reference to FIG. 1, which is presently being sold by Physio-Control, Inc. under the trademark Lucas®.

A CPR system 100 includes components that form a retention structure. These components include a central member 141, a first leg 121, a second leg 122 and a back plate 110. Central member 141 is coupled with first leg 121 and with second leg 122 via joints 181, 182 respectively. In fact, first leg 121 and second leg 122 can be partly rotated around joints 181, 182 with respect to central member 141. This rotation can help minimize the overall volume of CPR system 100, for easier storage at times when it is not used. In addition, the far ends of legs 121, 122 can become coupled with edges 131, 132 of back plate 110.

These couplings form the retention structure that retains the patient. In this particular case, central member 141, first leg 121, second leg 122 and back plate 110 form a closed loop, in which the patient is retained. For storage, back plate 110 can be uncoupled from legs 121, 121, which in turn can be further rotated so that their edges are brought closer to each other.

Central member 141 includes a battery that stores energy, a motor that receives the energy from the battery, and a compression mechanism that can be driven by the motor. The compression mechanism is driven up and down by the motor using a rack and pinion gear. The compression mechanism includes a piston 148 that emerges from central member 141, and can compress and release the patient's chest. Piston 148 is sometimes called a plunger. Here, piston 148 terminates in a suction cup 199 for active decompression. In this case the battery, the motor and the rack and pinion gear are not shown, because they are completely within a housing of central member 141.

Figure 2:
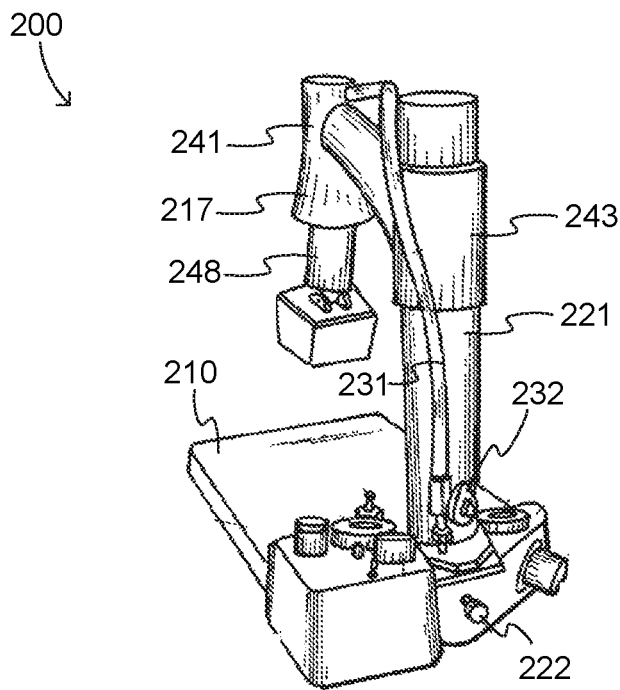
FIG. 2 shows elements of a diagram in a prior art reference for a CPR system.

FIG. 2 shows elements of a diagram of prior U.S. Pat. No. 4,326,507. In particular, FIG. 2 of the present document repeats selected features of that prior patent's FIG. 1. Specifically, in the present document, FIG. 2 shows another CPR system 200 having a platform 210, which operates as at least part of a patient retention structure. More particularly, the patient (not shown) may be placed supine on platform 210. A vertical removable upstanding column or support 221 is attached to the edge of platform 210, thus rising next to the patient. A releasable collar 243 supports an overhanging beam or arm 241 over platform 210. A piston plunger 248 emerges from overhanging beam or arm 241, and forms a compression mechanism for compressing downwards the chest of the patient who is supine on platform 210. In particular, piston plunger 248 is pneumatically operable to shift towards platform 210. The only power source required is an external source of compressed gas, normally oxygen, which is connected to the unit by a gas hose attached to a fixed connector. Pressurized oxygen passes through the compressor control valve assembly 222 inside the cardiac compressor platform, and then through hose 231 that extends to the upper end of a cylinder 217. A manual shutoff valve 232 may be provided to turn off the cardiac compressor manually. Such valves, therefore, can be drivers that drive the compression mechanism, etc.

Figure 3:
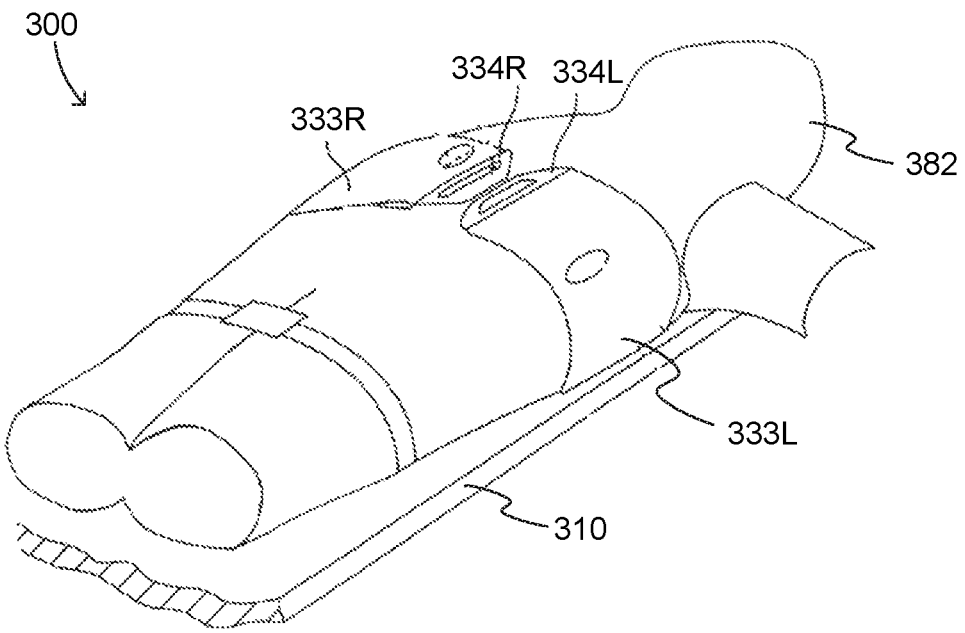
FIG. 3 shows elements of a diagram in another prior art reference for a CPR system.

FIG. 3 shows elements of a diagram of prior U.S. Pat. No. 6,939,315. In particular, FIG. 3 of the present document repeats selected features of that prior patent's FIG. 6. Specifically, in the present document, FIG. 3 shows another CPR system 300 having a platform 310, on which a patient 382 may be placed supine. A left side 333L of a chest compression belt terminates in a left buckle 334L, and a right side 333R of the chest compression belt terminates in a right buckle 334R. The chest compression belt can be buckled by joining left buckle 334L together with right buckle 334R. A spool (not shown in this FIG. 3) can collect and release the belt formed by left side 333L and right side 333R, and thus forms a compression mechanism. In fact, a driver motor (also not shown in this FIG. 3) can control the spool so as to retract and release the buckled belt, in order to cause the CPR chest compressions and releases.

Embodiments are now described in more detail.

Figure 4:
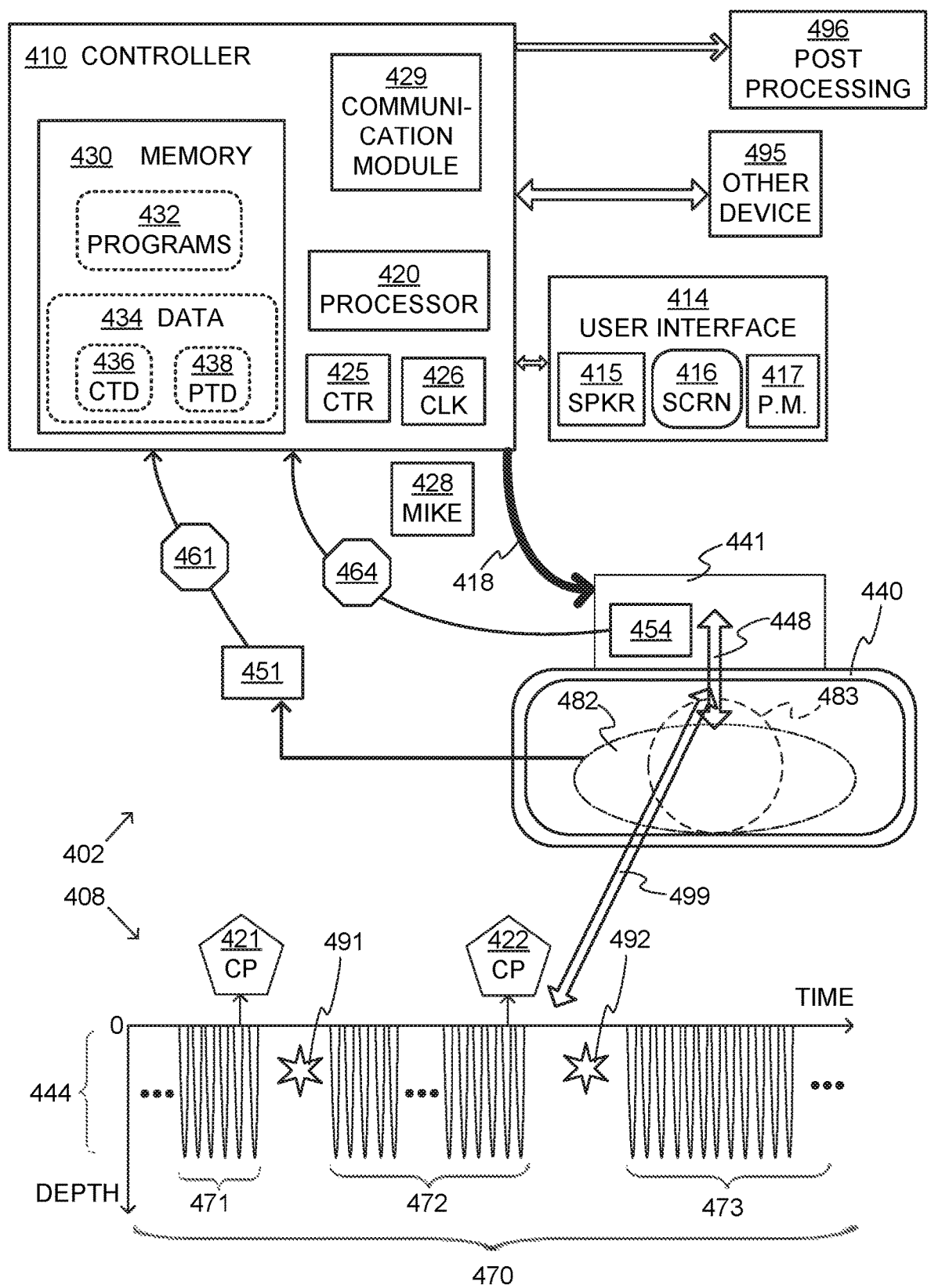
FIG. 4 is a diagram conceptually showing aspects of a CPR system in cooperation with a time diagram for a sample sequence of CPR chest compressions of the CPR system according to embodiments.

FIG. 4 is a composite, made of cooperating diagrams 402 and 408, which are bridged by an arrow 499. Diagram 402 shows components of a CPR system according to embodiments. This CPR system can be usable by a rescuer (not shown), who is also sometimes called an attendant. This CPR system can be usable by the rescuer to care for a patient 482, whose head is shown as 483.

More particularly, the components of diagram 402 include an abstracted retention structure 440 of a CPR chest compression machine. The rescuer places patient 482 supine within retention structure 440, and thus retention structure 440 retains the body of patient 482. While retention structure 440 typically reaches the chest and the back of patient 482, it often does not reach the head 483.

The components of diagram 402 also include a compression mechanism 448, which can be attached to retention structure 440. Compression mechanism 448 can be configured to perform CPR compressions to the chest of patient 482, and then releases after the CPR compressions.

The components of diagram 402 also include a driver 441. Driver 441 can be configured to control compression mechanism 448 automatically. This controlling may be such that the compression mechanism performs, while the body is thus retained in retention structure 440, automatically CPR compressions to the chest alternating with releases of the CPR compressions. The CPR compressions can be applied downwards, and cause the chest to become compressed by at least 2 cm from its initial resting height, and often deeper, consistently with the CPR Guidelines.

The combination of retention structure 440, compression mechanism 448 and driver 441 is often called a CPR machine, and may be implemented in a number of ways. For example, three such ways were described in FIG.s 1-3 of this document.

The components of diagram 402 may further include a controller 410. Driver 441 may be controlled by controller 410, and/or be considered to include controller 410, according to embodiments.

Controller 410 may include a processor 420. Processor 420 can be implemented in a number of ways, such as with one or more microprocessors, general purpose processors, microcontrollers, digital signal processors (DSPs), application specific integration circuits (ASICs), programmable logic circuits, programmable logic devices, etc. While specific uses are described for processor 420, it will be understood that processor 420 can either be standalone for these specific uses, or also perform other acts, operations or process steps.

Controller 410 may also include devices like a counter CTR 425 that is configured to count events, and a time keeping mechanism CLK 426 that is configured to keep time. These may be stand-alone devices, or implemented as functionalities of processor 420, or both.

In some embodiments controller 410 additionally includes a memory 430 coupled with processor 420. Memory 430 can be implemented by one or more memory chips, volatile memories, non-volatile memories (NVM), read only memories (ROM), random access memories (RAM), magnetic disk storage media, optical storage media, smart cards, flash memory devices, etc. Memory 430 can be thus a non-transitory storage medium that stores programs 432, which contain instructions for machines. Programs 432 can be configured to be read by processor 420, and be executed upon reading. Executing is performed by physical manipulations of physical quantities, and may result in functions, processes, actions, operations and/or methods to be performed, and/or processor 420 to cause other devices or components to perform such functions, processes, actions, operations and/or methods. Often, for the sake of convenience only, it is preferred to implement and describe a program as various interconnected distinct software modules or features, individually and collectively also known as software. This is not necessary, however, and there may be cases where modules are equivalently aggregated into a single program. In some instances, software is combined with hardware in a mix called firmware.

While one or more specific uses are described for memory 430, it will be understood that memory 430 can further hold data 434, such as event data, patient data, data of the CPR machine, and so on. For example, data gathered according to embodiments could be aggregated in a database over a period of months or years, and be used later to search for evidence that one pattern of CPR is more effective (in terms of a criterion) over others, of course correlating with the patient. Data could be de-identified so as to protect the patient's privacy. If so, then what is learned could be used to adapt the devices to employ the more effective pattern either continuously or at least as one of their operating modes. Data 434 can include a value 436 for a check time duration, and a value 438 for a pause time duration, the use of which will be understood later in this document.

Controller 410 may further include a communication module 429. Communication module 429 may transmit data 434 to a post-processing module 496. Alternately, data 434 may also be transferred via removable storage such as a flash drive. Post-processing module 496 may be part of a medical system network in the cloud, a server such as in the LIFENET® system, etc. While in module 496, data 434 can be used in post-event analysis. Such analysis may reveal how the CPR machine was used, whether it was used properly, and to find ways to improve future sessions, etc.

Communication module 429 may further communicate with an other device 495. Other device 495 can be a defibrillator, a monitor, a monitor-defibrillator, a ventilator, a capnography device, or any other medical device. Communication between communication module 429 and other device 495 could be direct, or relayed through a tablet or a monitor-defibrillator. Therapy from other device 495, such as ventilation or defibrillation shocks, can be coordinated and/or synchronized with the operation of the CPR machine. For example, compression mechanism 448 may pause the compressions for delivery of a defibrillation shock, afterwards detection of ECG, and the decision of whether its operation needs to be restarted. For instance, if the defibrillation shock has been successful, then operation of the CPR machine might not need to be restarted. Examples are also given in U.S. Pat. No. 7,308,304, which is hereby incorporated by reference.

The components also include a user interface 414. User interface 414 may be physically coupled or communicatively coupled with controller 410 via communication module 429. If communicatively coupled, this would mean that devices, features and implementations of user interface 414 could be provided, for example, in a smartphone or tablet computer or other device that is communicatively coupled with controller 410. This coupling can be by wire or wireless. Any of these wireless communications may be implemented by Bluetooth®, Wi-Fi, cellular, near field communications, etc.

User interface 414 may be used for receiving user instructions and settings from the rescuer or medical director, for outputting data, for alerting the rescuer, etc. Accordingly, user interface 414 may include one or more devices such as a keyboard, a speaker 415, a screen or touchscreen 416, a microphone, a dial, a knob, a switch, etc. Of those, output devices can be those that emit or output, for the rescuer, human-perceptible indications such as sounds, lights, images, tactile outputs, and so on.

Controller 410 can be configured to control driver 441 according to embodiments. Controlling is indicated by arrow 418, and can be implemented by wired or wireless signals and so on. Accordingly, compressions can be performed on the chest of patient 482 as controlled by controller 410.

In some embodiments, controller 410 adjusts its operation by receiving inputs about the patient. For example, a force sensor 454 can be configured to detect a force/motion relationship of the CPR compressions. Force sensor 454 can be further configured to output a force signal 464, which is indicative of a dynamic value of the force/motion relationship.

For another example, one or more parameter sensors 451 can be configured to detect a physiological parameter about the patient, and to output a parameter sensor signal 461 that is indicative of a dynamic value of the parameter. Such physiological parameters of the patient may include, for example, airway $CO_2$ partial pressure, ventilation measured as end tidal $CO_2$, signals indicating Return Of Spontaneous Circulation (ROSC) detection, pulse oximetry, blood pressure, arterial systolic blood pressure (ASBP), blood oxygen saturation ($SpO_2$), temperature, detection of pulse, etc.

Controller 410 may be implemented together with retention structure 440, in a single CPR chest compression machine. In such embodiments, the passing of one or more of signals 461, 464 and those of arrow 418 can be advantageously internal to such a CPR chest compression machine. Alternately, controller 410 may be hosted by a different machine, which communicates with communication module 429, etc.

As such, the CPR compressions can be performed in certain sequences according to embodiments. Some sample sequences are now described, while the invention may be practiced also by additional sequences.

Diagram 408 is a time diagram of CPR compressions and releases 444 along a time axis. The CPR compressions and releases 444 are shown along a vertical axis as changes in elevation. Each CPR compression is depicted as a stroke in the downward direction—given that the patient is supine—and each corresponding release is depicted as an upwards stroke. This is a direct representation for embodiments that use a plunger, and still an apt one for embodiments that use a belt. While diagram 408 thus uses the vertical negative semi-axis for the elevation, the positive semi-axis is not used this way. This is not limiting for other drawings, however, as will be seen later in this document.

In diagram 408, the strokes thus begin from the time axis and end at the time axis. The time axis is thus considered the "zero" height or reference level. That zero height could be the chest resting height, at least in the beginning of the session.

The downward strokes reach depths that can compress the patient chest. In diagram 408 all strokes are shown to reach the same depth, but that is only for simplicity—in fact the depths could be different among the strokes. In embodiments, most of the CPR compressions cause the chest to become compressed by at least 2 cm from its initial resting height, and deeper as mentioned above.

Diagram 408 depicts a certain sequence 470 of the CPR compressions according to embodiments. Sequence 470 can be part of a single resuscitation event for patient 482.

Sequence 470 includes a first group 471 of the CPR compressions. Only some of the compressions of first group 471 are shown. It will be observed that, within first group 471, the CPR compressions and releases 444 are shown occurring at regular time intervals, which would mean that they have a single frequency. This is only for purposes of illustration, however, and the time intervals could be irregular. Moreover, there are very short inter-stroke pauses between a release and the successive compression of a group, which are of course different from the pauses described elsewhere in this document.

First group 471 includes at least 120 of the CPR compressions. The person skilled in the art will recognize that, even if the compressions are performed at the rate of 80 cpm with no interruptions, 120 of the CPR compressions of first group 471 will require 1.5 min to be performed. "cpm" stands for compressions per minute; instead of "cpm", sometimes in the industry the term "bpm" is used for the equivalent beats per minute of the heart that the CPR machine effectuates. At the higher rate of 100 cpm, the same number of compressions may require somewhat less time. In embodiments, first group 471 may include more compressions, and/or last longer, for example a few minutes such as 2 to 4 min.

After first group 471, sequence 470 may include a check pause 491 from the CPR compressions. Check pause 491 is a pause during which the rescuer is expected to check the patient. Check pause 491 is a portion of sequence 470 that lasts at least 5 sec or maybe longer, such as 10-20 sec.

During check pause 491, the chest does not become compressed as during first group 471. In fact, in embodiments, during check pause 491 the CPR machine does not move at all, so as to instill confidence in the rescuer that it is safe to examine patient 482 closely without becoming caught in the CPR machine. It will be observed that, for ease of explanation, a star 491 is used in diagram 408 affirmatively as an icon to denote a pause, which could amount to even complete motionlessness by the CPR machine. Check pause 491 has an end when considered as an event, which means that at some time check pause 491 comes to an end, elapses.

In some embodiments, check pause 491 starts when the compression mechanism has completed a release. These are also the embodiments shown in FIG. 4. In other embodiments, the compression mechanism can be at a compression, and remain so during check pause 491. Additional embodiments are now described.

Figure 5:
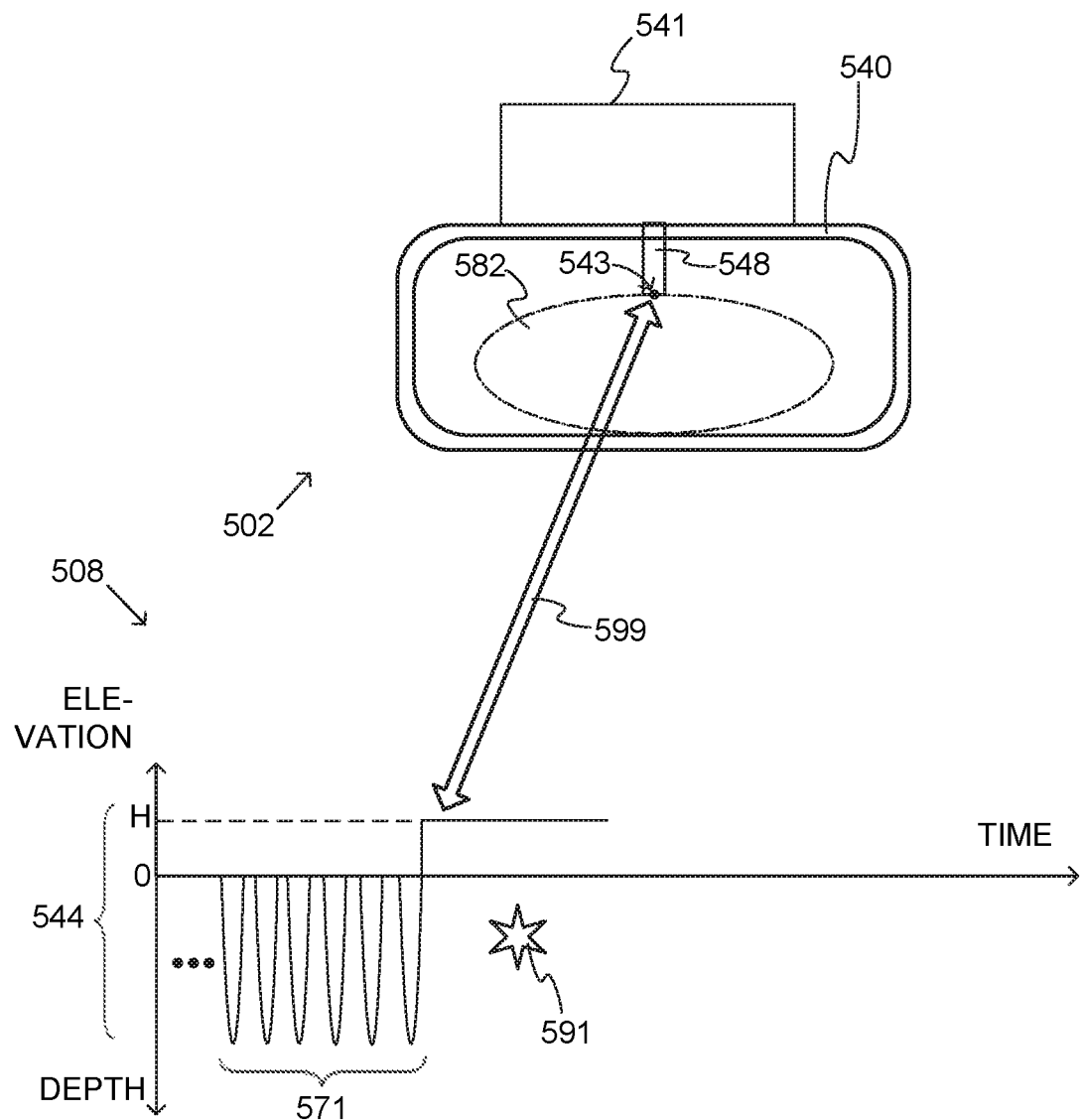
FIG. 5 shows details of a compression mechanism and its behavior during a pause according to embodiments, by using versions of the cooperating diagrams of FIG. 4.

FIG. 5 shows two cooperating diagrams 502, 508 that repeat aspects of diagrams 402, 408 of FIG. 4. Diagram 508 is bridged with diagram 502 by an arrow 599.

Diagram 502 shows a retention structure 540 that retains a patient 582. A driver 541 controls a compression mechanism that includes a plunger 548. In this embodiment, plunger 548 does not have a suction cup at the end, although it could.

A specific point 543 of plunger 548 is also indicated. Specific point 543 can be chosen anywhere on plunger 548; and it is arbitrarily chosen to be at the lowest point of plunger 548, so that its time trajectory will match the compression depth during the compressions and releases.

Diagram 508 is a time diagram that shows the depths of CPR compressions and releases 544. After a first group 571, a first check pause 591 starts. Given the above, diagram 508 also shows a time diagram of the elevation of specific point 543, during first group 571. As such, specific point 543 starts the compressions from a first elevation, namely zero.

During check pause 591, however, plunger 548 is lifted higher than the chest resting height, and therefore specific point 543 is automatically lifted by a distance H from the first elevation, or from the resting height of the patient's chest. This distance H can be at least 3 cm, or even a complete retraction of plunger 548 to its off position.

Returning to FIG. 4, upon the end of check pause 491, sequence 470 may include a second group 472 of the CPR compressions. After that, sequence 470 may further include a second check pause 492 and a third group 473 of the CPR compressions.

In some embodiments, a CPR system may further remind the rescuer to check patient 482, during such check pauses. Examples are now described.

In some embodiments, user interface 414 can be configured to output one or more human-perceptible check patient prompts CP 421, CP 422. These check patient prompts are shown in FIG. 4 above the time axis. It will be appreciated that check patient prompts CP 421, CP 422 are output shortly before first and second check pauses 491, 492, and can remind the rescuer to check patient 482 for a condition other than ventilating the patient. In other words, these check pauses are not pauses for ventilation, which can last up to 2-3 sec.

In embodiments, check patient prompts CP 421, CP 422 are output responsive to a check patient condition becoming met. A check patient condition can be defined in a number of ways, and a number of examples are now given.

For a first example, a check patient condition can include that a threshold number of the CPR compressions have been performed in a group, for example since a previous pause that concluded that lasted at least 3 sec, or 4 sec, etc. That threshold number could be at least 120. In the example of FIG. 4 second group 472 is deemed to have at least 120 compressions, or a number large enough for a few minutes to have passed, such as 2-5 minutes. A number of the CPR compressions in second group 472 can be counted by counter 425, and the patient check condition can become met when the counted number reaches the threshold number. In embodiments, the counter may become re-initialized after a pause in the CPR compressions that has lasted at least 3 sec, and so on.

Figure 6:
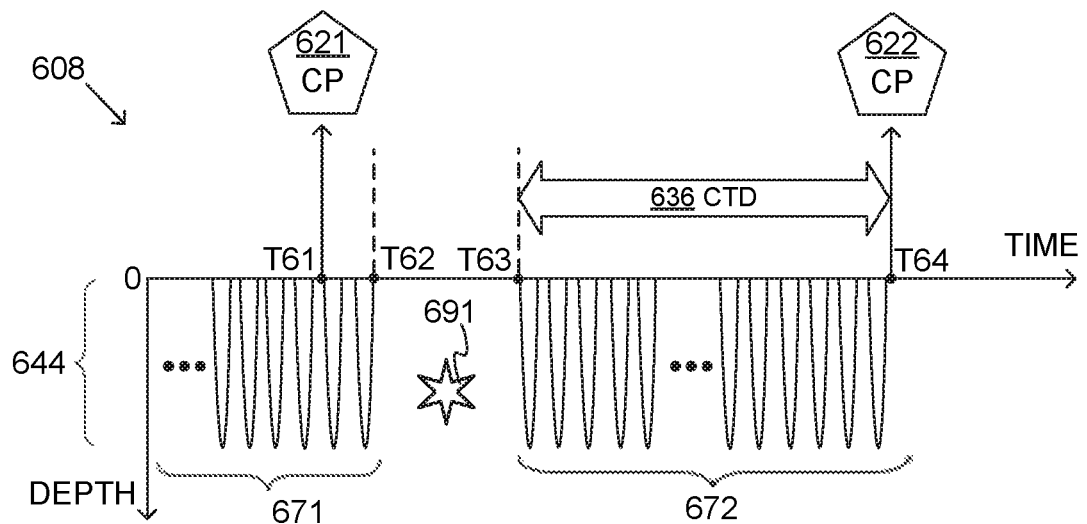
FIG. 6 is a time diagram of a sample sequence of CPR chest compressions and a check patient prompt according to embodiments.

Referring now to FIG. 6, a second example of a check patient condition can be explicitly in terms of time passing. FIG. 6 shows a time diagram 608 of CPR chest compressions and releases 644. A first group 671 is followed by a check pause 691, which is then followed by a second group 672 as part of the certain sequence. At time intercept T61, a first check patient prompt CP 621 is output. Time intercept T61 can also be called more simply time T61, and so on with all other time intercepts. Check pause 691 lasts between times T62 and T63. In other words, the end of check pause 691 occurs at time T63, at which time the CPR compressions of the next group restart.

In this second example, time can be kept by time keeping mechanism CLK 426 for the second group 672 of the CPR compressions. And, the patient check condition can become met when the kept time exceeds a check time duration, which is shown as a duration CTD 636 in FIG. 6. As such, second check patient prompt CP 622 can be output at time T64. The check time duration can last at least 1.5 min, and preferably 3-5 min. In embodiments, the time keeping mechanism can become re-initialized after a pause in the CPR compressions that has lasted at least 3 sec, etc.

The check time duration is, therefore, a frequency by which a rescuer is reminded, by the check patient prompt, to check the patient. In some embodiments, the value of the check time duration can be adjusted. As was seen in FIG. 4, a value 436 for the check time duration can be stored in memory 430, and can be adjusted at that location.

In some embodiments, communication module 429 is configured to receive a remote check time duration input. The stored value CTD 436 for the check time duration can then become adjusted responsive to the received remote check time duration input.

Figure 7:
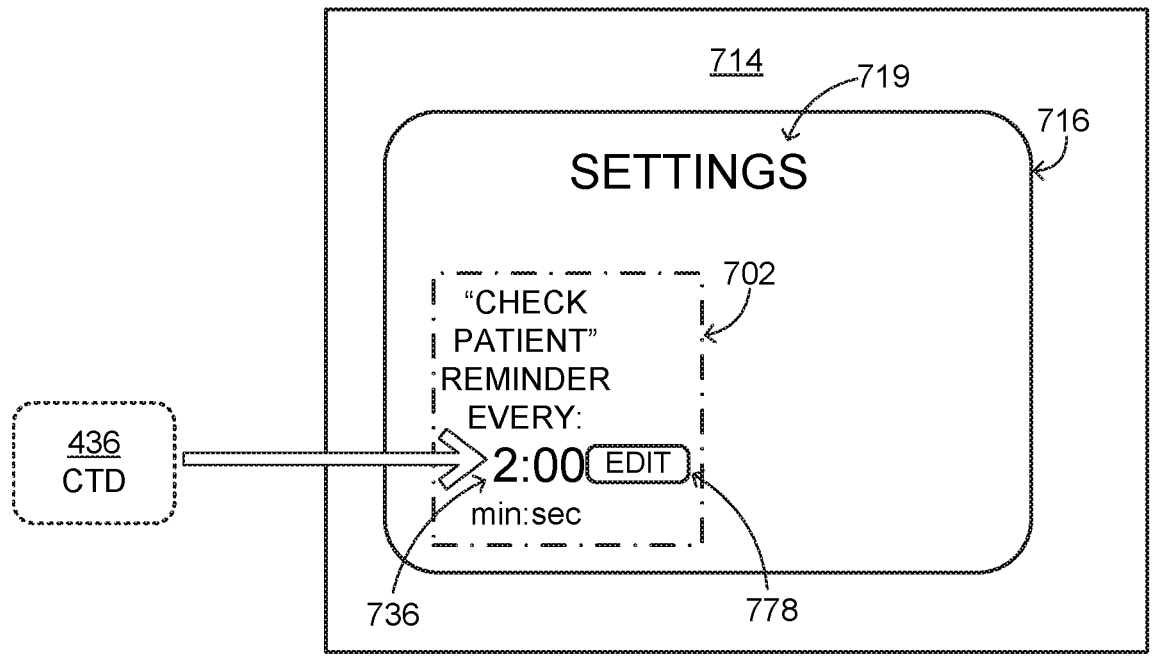
FIG. 7 is a diagram of a sample portion of a user interface of a CPR system for a person to adjust a frequency of outputting a check patient prompt, such as the check patient prompt of FIG. 6, according to embodiments.

Referring now to FIG. 7, a user interface 714 is an embodiment of user interface 414. User interface 714 is further configured to receive a local check time duration input from a person like the rescuer or a medical director. Then the stored value CTD 436 for the check time duration can become adjusted responsive to the received local check time duration input. For example, a touchscreen 716 can have a "SETTINGS" heading 719. In addition, a section 702 on touchscreen 716 can have a display 736 that shows the stored value CTD 436. In the example of FIG. 7, that value is 2:00 min. Moreover, an "EDIT" button 778 can be provided for editing the value. Touching "EDIT" button 778 can be a way to receive the local check time duration input, in the form of a new value that will become stored as value CTD 436. Touching "EDIT" button 778 can present a keypad, up/down arrows, etc.

Figure 8:
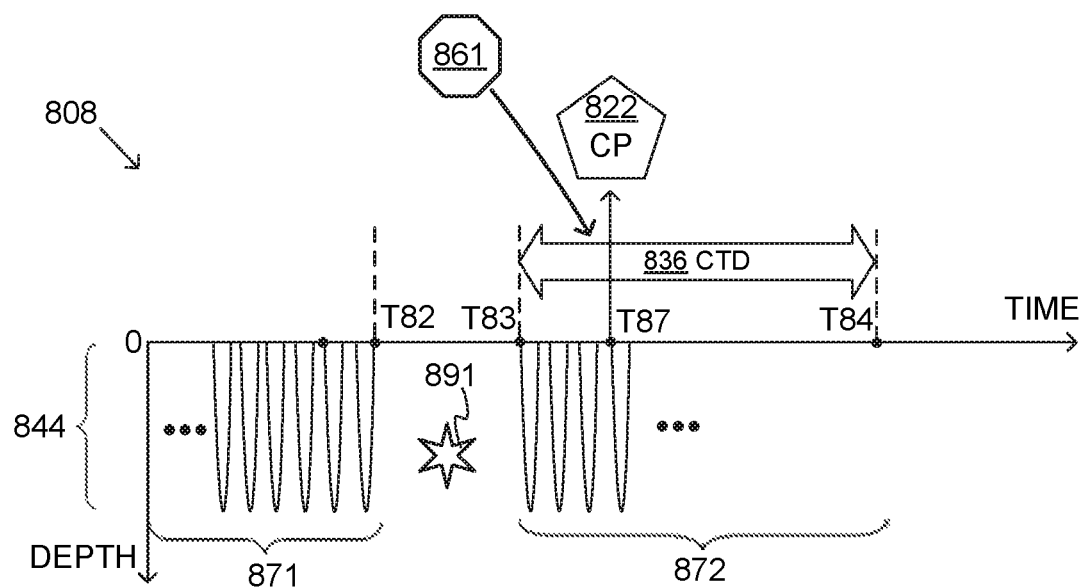
FIG. 8 is a time diagram of a sample sequence of CPR chest compressions in which a check patient prompt is output long before a check time duration, according to embodiments.

Referring now to FIG. 8, a third example of a check patient condition can be if a change is detected in the patient condition. FIG. 8 shows a time diagram 808 of CPR chest compressions and releases 844. A first group 871 is followed by a check pause 891 and then by a second group 872. Check pause 891 lasts between times T82 and T83. In other words, the end of check pause 891 occurs at time T83.

As things are, a check time duration CTD 836 ends at time T84. This, however, is not necessarily the time that the CPR compressions restart in the form of second group 872. In fact, in this example a check patient prompt CP 822 is output long before time T84, namely at a substantially earlier time T87, as a result of a change in the patient condition. This means that a number of the CPR compressions in second group 872 will not have been performed yet; and, if the rescuer reacts timely by pausing the CPR system, they may not be performed at all. Check patient prompt CP 822 can be thus output earlier in a number of ways.

In some embodiments, check patient condition 861 includes that a pause instruction has been received from other device 495. Indeed, communication module 429 can be configured to receive such a pause instruction from other device 495. Of course, such a pause instruction can be synchronized with what other device 495 will attempt to do.

There are a number of possibilities for generating such a pause instruction. For example, other device 495 can be a ventilator that needs to deliver large sustained breaths to recruit or re-inflate collapsed alveoli. Then the pause instruction can be repeated 5 minutes after alveoli recruitment, for a repeat of that recruitment maneuver. Or, the same effort could be done with individual positive pressure breaths, although the frequency of these would need to be limited, so as to avoid pausing the compressions too much.

For another example, other device 495 can be an ultrasound machine that generates such a pause instruction, so that it can perform ultrasound imaging. This could be used for example to facilitate imaging of the heart to see if there is heart wall motion, which may indicate the potential of the heart to pump blood, without introducing a long pause in compressions.

For one more example, other device 495 can be a defibrillator that might instruct to pause the compressions so that it will defibrillate, and allow enough time for recovery to be detected. For example, a monitor/defibrillator could perform a computer analysis of the ECG, and the pause could be just long enough to complete the analysis.

At the very least, it may be desired to avoid having a compression immediately (e.g. within the first 1 or 2 seconds) after the shock that might mechanically stimulate the heart. This would be so as to prevent the compressions from interfering with the post-shock electrical activation patterns of a shock that was going to terminate VF.

In response to a pause instruction, a compression mechanism that includes a plunger pauses after completing its current upstroke (if the shock occurs during an up-stroke), or aborts an in-progress down-stroke (and resets to the max upstroke position for resumption of compressions after the pause). The pause duration for these shock-associated pauses could be, for example, in the range of 1-3 seconds, or alternately could involve skipping 1-3 compressions that would have been delivered, while maintaining the overall compression cadence. Or, a longer check patient pause may be allowed, for the rescuer to check manually for rhythm.

The pause instruction may further encode a pause time duration, and the check pause may last as specified by the encoded pause time duration. The encoded pause time duration may be a suggested minimum time for an impending operation by other device 495, or for a check due to something sensed by other device 495, and so on. The encoded pause time duration may further include a not-to-exceed value for resuming the CPR compressions, and so on. Moreover, a periodicity maybe communicated by other device 495, as to how often the pauses should occur, and so on. In addition, a pause instruction may be followed with instructions about shortening the pause or extending the pause, as described elsewhere in this document.

In some embodiments, check patient condition 861 includes that a stoppage criterion, also known as stopping criterion, becomes met by the dynamic value of the parameter indicated in parameter sensor signal 461. That, even if the threshold number of the CPR compressions in second group 872 has not been performed yet, which may equivalently mean that the check time duration CTD 836 has not passed yet. The stoppage criterion can be that the patient's vital signs can exhibit a risk, for example as detected by sensors 451, 454, etc. In some of these embodiments, the parameter of patient 482 is detected while second group 872 of the CPR compressions is being performed. Examples are given in pending U.S. patent application Ser. No. 14/942,835, filed on Nov. 16, 2015, and published as document No. US 20160067140 on Mar. 10, 2016, and which is hereby incorporated by reference. Or, the pause may happen by another machine to check. Additional examples are given below.

In some embodiments, the parameter of the patient includes an Electrocardiogram (ECG). Sensing of the ECG could be facilitated or enhanced by use of a filtering algorithm to substantially reduce or eliminate the ECG artifact caused by the mechanical chest compressions. In such embodiments, the stoppage criterion can become met if a dynamic value of the ECG includes a QRS complex. Or that an aspect of a QRS morphology narrows by more than a certain amount within a time period. Or, the stoppage criterion can become met if a dynamic value of the ECG indicates that a patient rhythm has changed from non-shockable to shockable, for example Ventricular Fibrillation. Or, the stoppage criterion can become met if a dynamic value of a heart rate measured from the ECG increases by more than a certain amount within a time period. Or, the stoppage criterion can become met if a dynamic value of the ECG that is synchronous with a dynamic value of the impedance fluctuates.

In some of these embodiments, the check patient condition includes that a stoppage criterion becomes met by the dynamic value after the second group of the CPR compressions has been performed uninterrupted for at least 1 min, and preferably longer than the check time duration or 2 min. In this manner, this functionality does not ever interfere with a usual resuscitation pattern of checking periodically; rather it could activate its "protection against prolonged un-recognition of ROSC" only when the CPR system has been performing uninterrupted compressions for a more prolonged interval.

In some embodiments, the parameter of the patient includes an airway $CO_2$ partial pressure. In such embodiments, the stoppage criterion may become met if a dynamic value of the airway $CO_2$ partial pressure exceeds a threshold, for example 50 mmHg.

In some embodiments, the parameter of the patient includes an airway end-tidal $CO_2$. In such embodiments, the stoppage criterion may become met if a dynamic value of the airway end-tidal $CO_2$ increases by more than a certain amount within a time period, for example if it increases by more than 20 mmHg within 1 min.

In some embodiments, the parameter of the patient includes a blood pressure. In such embodiments, the stoppage criterion may become met if a dynamic value of the blood pressure reaches a threshold. If there is any appreciable blood pressure during the time when compressions are paused, a check for return of spontaneous circulation (ROSC) would be indicated. Accordingly, when using a pressure sensor in an artery, a diastolic pressure above even 20 mmHg would be a sign of circulation, and a systolic of 30 or 40 mmHg would similarly indicate likely ROSC. And, even with a less high quality way of reading blood pressure, essentially any indication of blood pressures above 30 mmHg may indicate ROSC.

In some embodiments, the parameter of the patient includes a regional oxygen saturation. In such embodiments, the stoppage criterion may become met if a dynamic value of the regional oxygen saturation reaches a threshold. Regional oxygen saturation ("rSO2") can be a percentage saturation of hemoglobin with oxygen, in tissue of the patient that is being monitored. For example, a cerebral oximeter can be applied to the patient's forehead, when the tissue of interest can be accordingly the part of the brain just under the skull. The reading of a cerebral oximeter may be expressed as percentage. That reading may be 70% or higher for a person with good blood flow to their brains, while it may be 30% for a patient in cardiac arrest.

It should be remembered that, unlike with pulse oximeters, cerebral oximeters are making a slower, steady-state measurement of (loosely) the color of the tissue, and do not require pulsatile blood flow to get a reading. The cerebral hemoglobin oxygen saturation is considered to be a measure of the balance between the supply and demand for oxygen in the tissue monitored.

In some embodiments, the retention structure includes one or more straps configured to be used by the rescuer to restrain a motion of the patient's body. For example, straps can be used to secure the patients arms "out of the way". Straps can also be used for the legs, if the patient is on a gurney, and a team of rescuers have to descend stairs, etc. These can be useful when moving the patient through doorways, while the CPR machine is strapped on the patient. If the patient were to regain consciousness and be unhappy about the chest compressions, they could try to pull their hands and arms out of the straps. In addition, the retention structure may include a force sensor configured to detect a change in the force applied to the strap. The force sensor can use, for example, a spring to detect tension, and be coupled in series with the strap. In such embodiments, the stoppage criterion becomes met if a detected change in the force applied to the strap reaches a threshold.

Figure 24:
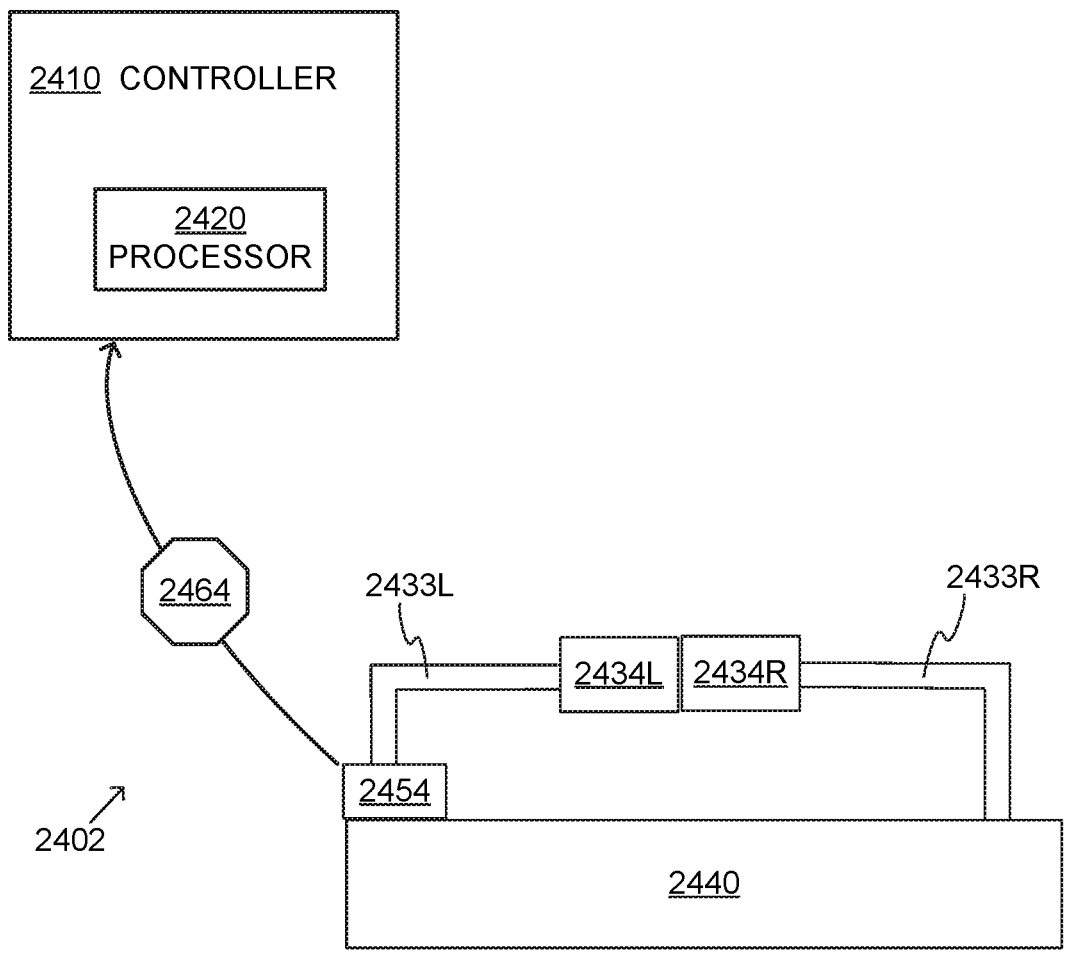
FIG. 24 is a diagram for illustrating a restraining strap coupled with a force sensor according to embodiments.

An example is shown in FIG. 24, where a diagram 2402 shows components of a CPR system. A controller 2410 includes a processor 2420, both of which can be as described above. A retention structure 2440 includes left strap 2433L with a left buckle 2434L. Retention structure 2440 also includes right strap 2433R with a right buckle 2434R that can become coupled to left buckle 2434L, so as to form a strap 2433L-2433R that restrains the patient's body. A force sensor 2454 is coupled serially between retention structure 2440 and left strap 2433L. Force sensor 2454 can detect a change in the force applied to the strap, and send a signal 2464 to controller 2410.

In some embodiments, the parameter sensor includes a defibrillation detector. Such can be, for example, as described in patent application US 20170021182 A1, which is hereby incorporated by reference. Or, an electrical device that already has a coil could be adapted accordingly. In such embodiments, the stoppage criterion may become met if a defibrillation was detected by the defibrillation detector. In such embodiments, a custom pause time duration could be further specified. A benefit of this approach is that it could allow close coordination of timing of re-initiation of chest compressions after the shock, without the need to have the chest compression machine and monitor-defibrillator in communication. So, for example, the chest compression machine and defibrillator could be made by different (and non-cooperating) manufacturers.

In some embodiments, the check patient condition 861 includes that a change in the force/motion relationship that is detected by force sensor 454 is above a threshold. Such a change could be, for example, due to a voluntary muscle contraction in the thorax, or indicative of a rib/sternum fracture, meriting attention from the rescuer. As per the above, a dynamic value of the force/motion relationship can be indicated by force signal 464. Again, that can happen even if the threshold number of the CPR compressions in second group 872 has not been performed yet, which may equivalently mean that the check time duration CTD 836 has not passed yet.

In some embodiments, the CPR system further includes a sound sensor 428, which can be configured to detect a sound of the patient. Sound sensor 428 is shown in FIG. 4 as not attached to anything, because it could be in different places. For example, sound sensor 428 could be part of user interface 414, retention structure 440, a separate microphone attached to the patient similarly to sensor 451, and so on. In such embodiments, the check patient condition could include that the detected sound is identified as the patient's vocalizing. Some sound recognition functionality, for example filtering and artificial intelligence, may be added to controller 410, so as to identify a sound as coming from the patient instead of being background noise.

In some embodiments, the CPR system further includes ways of detecting strain in straps holding the patient's torso, arms, etc., especially while the patient's chest is not being compressed. Change in the strain, especially while the patient's chest is not compressed, may indicate motion by the patient, which in turn may indicate restoration of some degree of consciousness. Again, such would merit attention from the rescuer. In such embodiments, the check patient condition could include that such a change in the strain is identified as patient motion.

There is a number of ways of outputting the check patient prompt. Being a human-perceptible indication, the check patient prompt can include a message spoken by speaker 415, or shown in screen 416, indicated by light sources lighting, and so on. A message spoken by speaker 415 has the advantage that it can be heard even if the rescuer is looking elsewhere at the time, possibly distracted by other tasks or evolving developments.

In such embodiments, the stoppage criterion can include other conditions. For example, the CPR system may detect that patient 482 has shifted within retention structure 440 and their position needs readjustment, and so on.

In such embodiments where a change is detected in the patient condition, the check patient prompt is preferably not the same as that of a usual reminder. Rather, it is preferred that, in such cases, the check patient prompt sounds differently, more like an alarm. The alarm maybe graduated or escalating, and can be user configurable in advance, and so on. In some embodiments, the check patient prompt includes a notification about the dynamic value of the parameter or about the stoppage criterion. In such embodiments, then, a sound or an image may indicate what the patient's change condition is.

As will be seen later in this document, in many embodiments the second group of performed CPR chest compressions ends, and is followed by a next check pause. In some of these embodiments, the check patient prompt includes a stopping count-down synchronized with a beginning of the next check pause. An example is now described.

Figure 9:
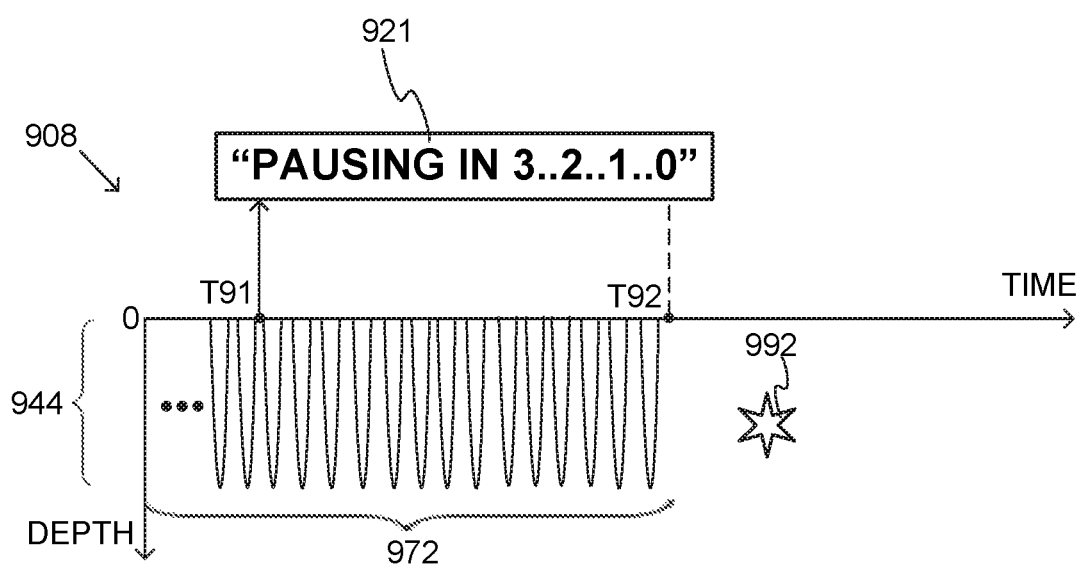
FIG. 9 is a time diagram of a sample sequence of CPR chest compressions, in which a check patient prompt, such as the check patient prompt of FIG. 6 includes a count-down according to embodiments.

Referring now to FIG. 9, a time diagram 908 shows CPR chest compressions and releases 944. A first group of the CPR compressions is not shown. A second group 972 ends at time T92, and is followed by a next check pause 992 that starts at T92. A check patient prompt 921 includes a stopping count-down that is synchronized with a beginning of the next check pause at time T92, and therefore with the end of the CPR compressions of group 972. Synchronization is attained by starting check patient prompt 921 at time T91, so it ends at time T92 as desired. Being a human-perceptible indication, the count-down can be visual, audible, or both. A count-up can be made instead of a count-down, and so on.

There is a number of ways in which the second group of performed CPR chest compressions 972 ends, and next check pause 992 begins, after check patient prompt 921 has been output. In some embodiments, the CPR machine pauses by itself automatically as part of the certain sequence, implicitly expecting that the rescuer will attend to the patient. In other embodiments, the check patient prompt is output as a reminder, but it is completely up to the rescuer to initiate the pause. Either way, after the pause the machine may restart automatically. Examples of such ways are now described.

In FIG. 4, diagram 408 showed an example of a second group 472 of CPR compressions, a second check pause 492, and a third group of CPR compressions. These are repeated now in more detail, so as to describe better the nature of the pause.

Figure 10:
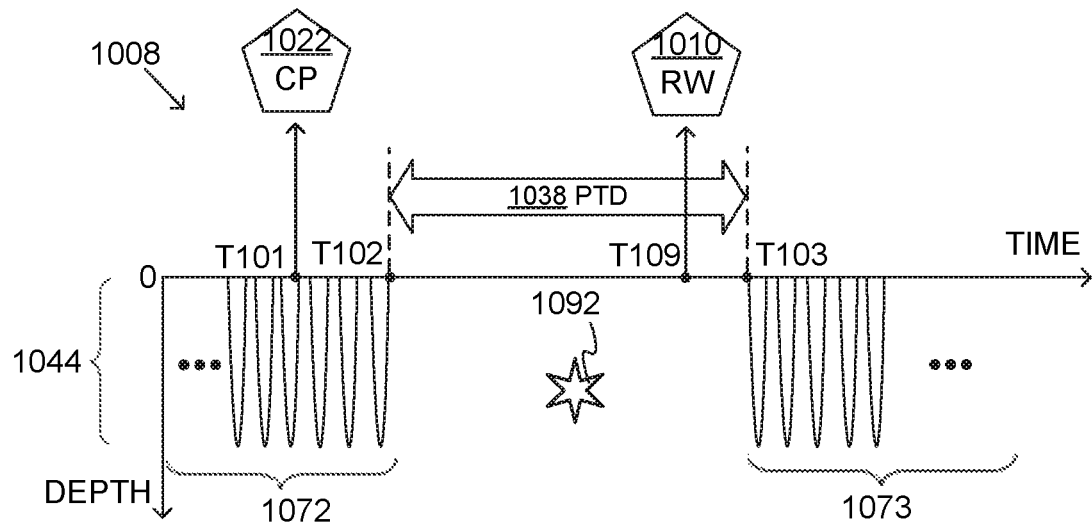
FIG. 10 is a time diagram of a sample sequence of CPR chest compressions that includes a pause, and in which a restart warning is output, according to embodiments.

FIG. 10 shows a time diagram 1008 of CPR chest compressions and releases 1044. A first group of CPR compressions, a first check patient prompt, and a first check pause are not shown. A second group 1072 is followed by a second check pause 1092, which is then followed by a third group 1073, as part of the certain sequence. A second check patient prompt 1022 is output at time T101.

Second check pause 1092 can be a pause from performing the CPR compressions. In particular, second check pause 1092 may start by pausing the performing the CPR compressions, in other words ending second group 1072 at T102, in connection with second check patient prompt 1022 being output. Second check pause 1092 may last for a pause time duration PTD 1038 of at least 5 sec, i.e. until T103. Then, upon an end of second check pause 1092 at T103, performing the CPR compressions maybe restarted or re-initiated, by starting a third group 1073 of the CPR compressions.

This assumes that, during second check pause 1092, the rescuer will indeed check the patient. This need not be assumed always. In some situations, if the rescuer would not check the patient, the CPR system might as well not pause at all! Accordingly, in some embodiments, user interface 414 further includes a pause means 417 that is configured to generate a pause input upon being actuated by the rescuer. The generated pause input can help confirm that rescuer will indeed check the patient during the second check pause. In such embodiments, second check pause 1092 does not start unless the pause input is indeed thus generated. Some pause means embodiments are described in more detail later in this document. In this case, such a pause means would have to be received validly, namely only after the check patient prompt is output, etc. Such can be within the settings of the CPR system, along with settings such as "do not pause automatically", etc.

The pause time duration is, therefore, the time interval given to the rescuer to check the patient. The pause time duration may advantageously be, for example, 5, 10, 15, or 20 sec for checking the patient. In some embodiments, its value can be adjusted. As was seen in FIG. 4, a value 438 for the pause time duration can be stored in memory 430, and can be adjusted at that location.

In some embodiments, communication module 429 is configured to receive a remote pause time duration input. The stored value PTD 438 for the pause time duration can then become adjusted responsive to the received remote pause time duration input.

Figure 11:
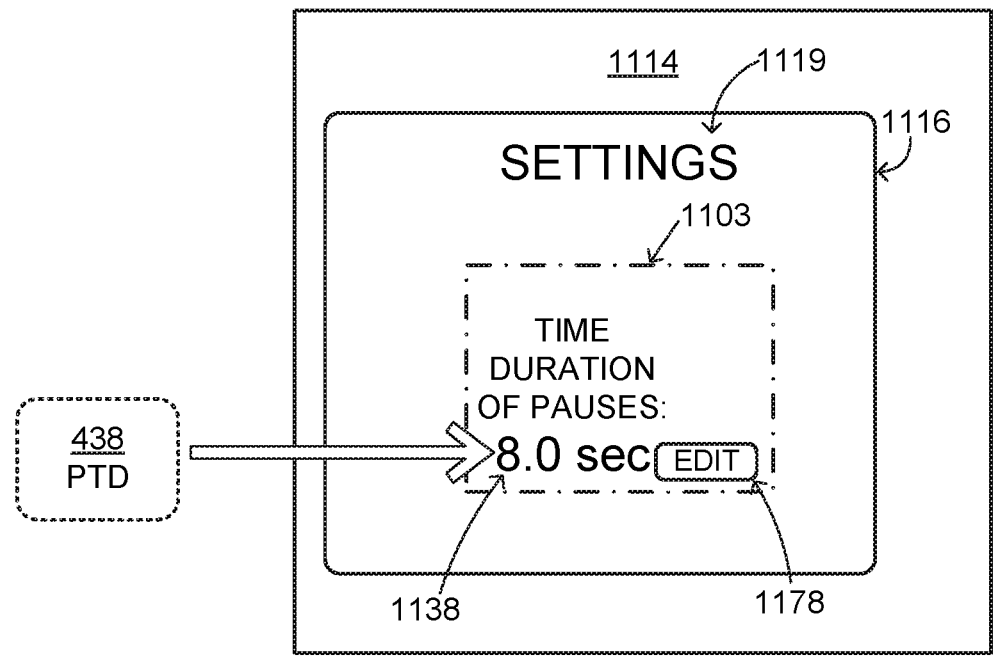
FIG. 11 is a diagram of a sample portion of a user interface of a CPR system for a person to adjust a pause time duration such as the pause time duration of FIG. 10, according to embodiments.

Referring now to FIG. 11, a user interface 1114 is an embodiment of user interface 414. User interface 1114 is further configured to receive a local pause time duration input from a person like the rescuer or a medical director. Then the stored value PTD 438 for the pause time duration can become adjusted responsive to the received local pause time duration input. For example, a touchscreen 1116 can have a "SETTINGS" heading 1119. In addition, a section 1103 on touchscreen 1116 can have a display 1138 that shows the stored value PTD 438. In the example of FIG. 11, that value is 8.0 sec. Moreover, an "EDIT" button 1178 can be provided for editing the value. Touching "EDIT" button 1178 can be the way to receive the local pause time duration input, in the form of a new value that will become the stored value PTD 438.

More embodiments are possible. For example, the user interface may include a "restart from pause" means that is configured to generate a restart input responsive to being actuated by the rescuer. The restart from pause means can be the same as a start means, or distinct from it. The generated restart input may be validated, for example be considered valid only if generated during the second check pause but before the pause time duration has passed. In such embodiments, the end of the second check pause may occur responsive to the restart input being generated, instead of when the pause time duration has passed. Moreover, value 438 for the pause time duration stored in memory 430 may become adjusted responsive to how long second check pause 1092 actually lasted, i.e. based on experience of this rescuer in this scenario.

As already mentioned above, after the check patient prompt has been output, in other embodiments the check patient prompt is output as a reminder, but it is completely incumbent upon the rescuer to initiate the pause. In such embodiments, user interface 414 further includes a pause means 417, of which multiple examples are given later in this document. As already mentioned above, pause means 417 can be configured to generate a pause input responsive to being actuated by the rescuer. In these embodiments, the CPR system expects that the rescuer would actuate pause means 417 upon the rescuer perceiving check patient prompts CP 421, CP 422, CP 1022, etc. And, if none is given, the compressions might as well not pause in some instances. In some embodiments there might be no pause anyway, even if the machine has been providing uninterrupted compressions for a sufficient number of minutes to normally trigger the automatic prompt or pause of the present invention, if the ECG rhythm is detected as incompatible with ROSC (asystole, Ventricular Fibrillation (VF), very slow/very wide-complex bradycardia).

In embodiments of FIG. 10, user interface 414 of FIG. 4 can be further configured to output, in conjunction with the end of check pause 1092, a human-perceptible restart warning 1010 to the rescuer about the end of check pause 1092. This restart warning 1010 would announce the impending restart of CPR compressions in next group 1073. Next group 1073 is the third group in FIG. 10, but this also applies to any restarting with a new group, such as with second group 472, and so on. The restart warning can be to the effect of reminding the rescuer to have cleared the CPR machine and left everything in order for the imminently following CPR compressions to be performed properly.

In some embodiments, the restart warning includes a restart count-down that is synchronized with the end of the check pause and, therefore, with the restarting of the performance of the CPR compressions. As such, the restart count-down warns about the performance of the next group of CPR compressions beginning imminently. An example is now described.

Figure 12:
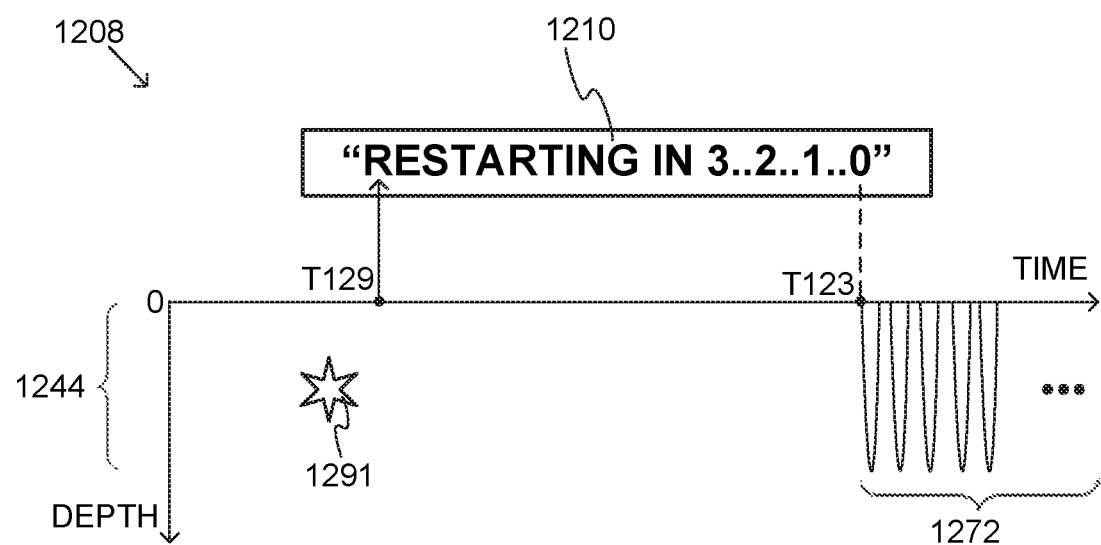
FIG. 12 is a time diagram of a sample sequence of CPR chest compressions, in which a restart warning, such as the restart warning of FIG. 10 includes a restart count-down according to embodiments.

Referring now to FIG. 12, a time diagram 1208 shows CPR chest compressions and releases 1244. A first group of the CPR compressions is not shown. A check pause 1291 ends at time T123, at which time a next group 1272 starts. In conjunction with the end of check pause 1291, a human-perceptible restart warning 1210 is output to the rescuer about the end of check pause 1291, and therefore also about the next group 1272 starting soon. Restart warning 1210 includes a restart count-down that is synchronized with the end of check pause 1291 at time T123. Synchronization is attained by starting restart warning 1210 at time T129, so it ends at time T123 as desired. Again, the count-down can be visual, audible, or both. A count-up can be output instead of a count-down, and so on.

Moreover, methods and algorithms are described below. These methods and algorithms are not necessarily inherently associated with any particular logic device or other apparatus. Rather, they are advantageously implemented by programs for use by a computing machine, such as a general-purpose computer, a special purpose computer, a microprocessor, etc. These algorithms are not necessarily purely mathematical, and are configured to address challenges particular to the problem solved, as will be apparent to a person skilled in the art. In embodiments, a non-transitory computer-readable storage medium stores one or more programs which, when executed by systems or devices according to embodiments, result in operations according to embodiments. Execution can be by a processor that reads the storage medium, etc.

This detailed description includes flowcharts, display images, algorithms, and symbolic representations of program operations within at least one computer readable medium. An economy is achieved in that a single set of flowcharts is used to describe both programs, and also methods. So, while flowcharts describe methods in terms of boxes, they also concurrently describe programs.

Methods are now described. These methods may be implemented or performed by embodiments described in this document.

Figure 13:
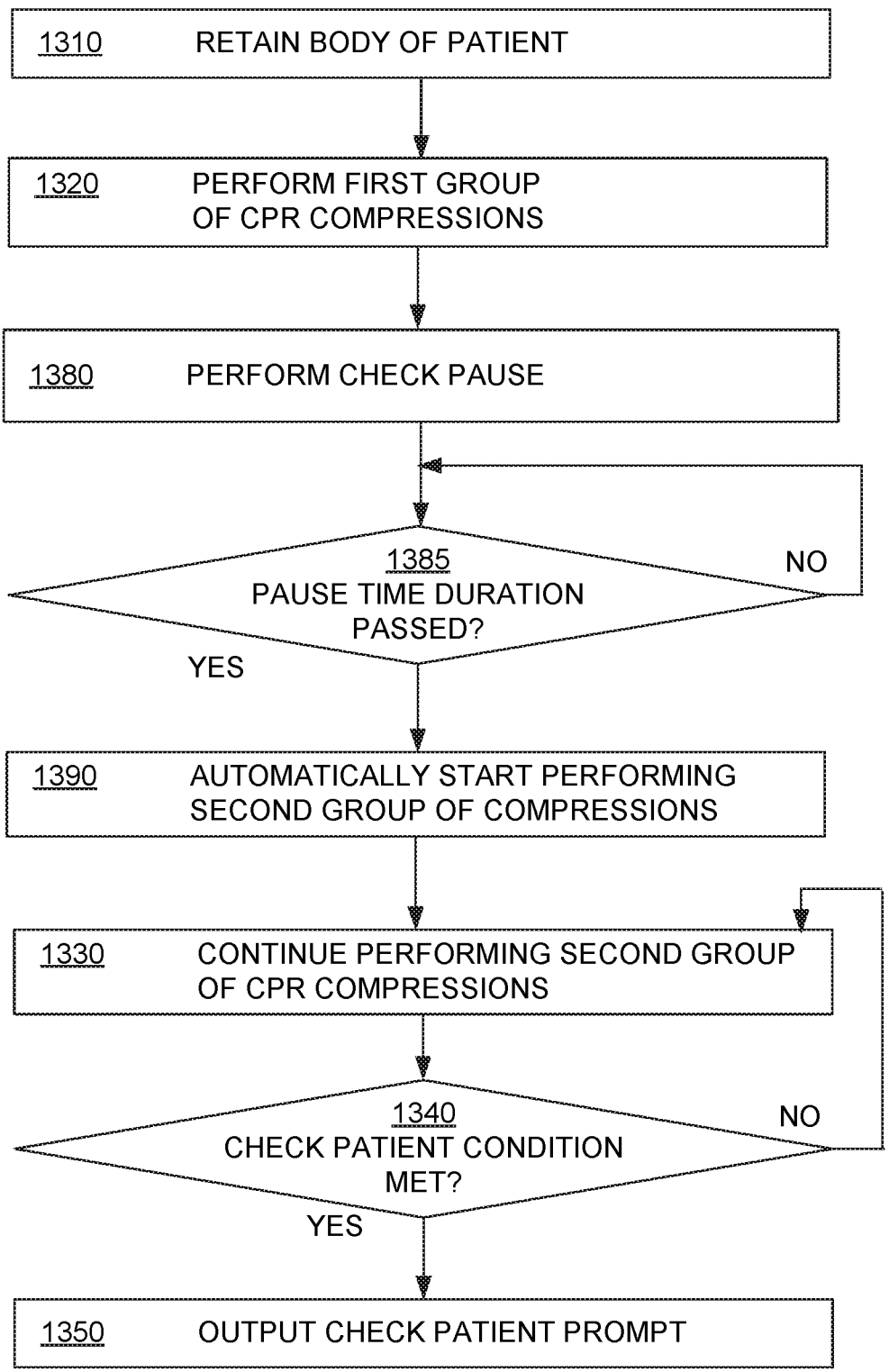
FIG. 13 is a flowchart for illustrating methods according to embodiments.

FIG. 13 shows a flowchart 1300 for describing methods according to embodiments. According to an operation 1310, the patient's body is retained. This can be performed by retention structure 440.

According to another operation 1320, a first group of at least 120 CPR compressions alternating with releases to the CPR compressions is performed. This first group can be performed by the compression mechanism to a chest of the body, while the body is thus retained. Most, if not all of the CPR compressions may cause the chest to become compressed by at least 2 cm.

According to a subsequent operation 1380, a check pause from performing the CPR compressions of the first group may then be performed. During the check pause the patient's chest does not become compressed as it was during the first group.

The check pause may last at least 5 sec. For example, according to a sample operation 1385, time can be kept until a pause time duration has passed.

Then, according to another operation 1390, upon an end of the check pause, a second group of the CPR compressions may start being performed. This amounts to restarting the compressions. According to another operation 1330, this second group of the CPR compressions may continue being performed.

According to another operation 1340, it can be determined whether or not a check patient condition has become met. The check patient condition can be as described above.

According to another operation 1350, a human-perceptible check patient prompt may be output by the user interface, responsive to the check patient condition becoming met at operation 1340. The check patient prompt may be as described elsewhere in the document.

A number of the previously described embodiments may further be applicable. For example, the compression mechanism may include a plunger. During operation 1320, a specific point of the plunger may start one of the compressions from a first elevation, while during operation 1385, the specific point can be automatically lifted by at least 3 cm from the first elevation.

For another example, the CPR system may include a counter, and the patient check condition may become met when a counted number of the CPR compressions in the second group reaches the threshold number.

Or, the CPR system may include a time keeping mechanism that keeps time for the second group of the CPR compressions, and the patient check condition could become met when the kept time exceeds a check time duration. And the stored value for the check time duration may be updated as per the above.

Figure 14:
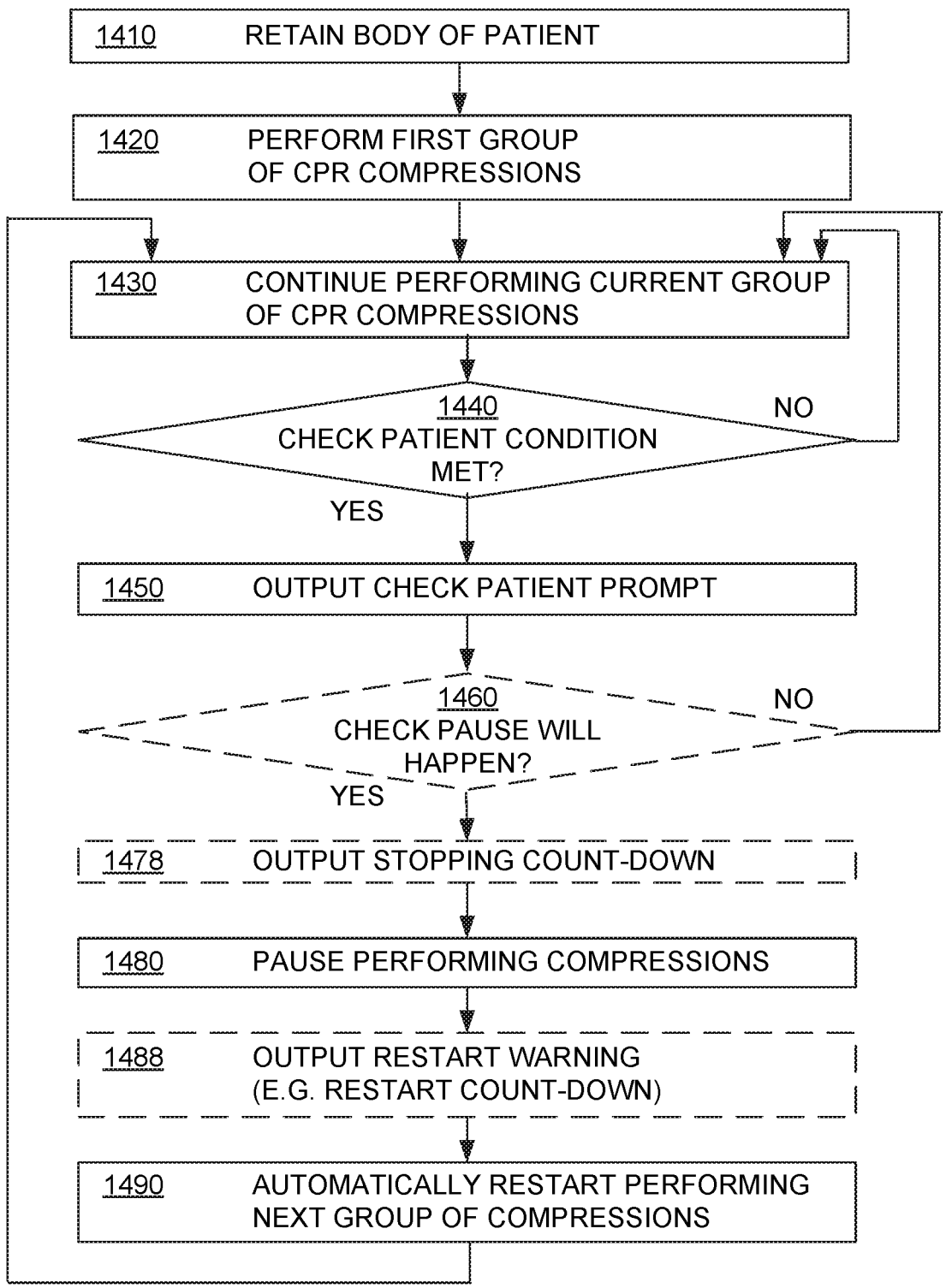
FIG. 14 is another flowchart for illustrating methods according to embodiments.

FIG. 14 shows a flowchart 1400 for describing methods according to embodiments. Flowchart 1400 presents embodiments that may be continuously implemented so that check patient prompts can be output for the rescuer substantially periodically, over a potentially long resuscitation event.

It will be recognized that many operations of flowchart 1400 are similar to operations of flowchart 1300 that are similarly numbered. For example, operations 1410, 1420, 1440, 1450 can be similar to operations 1310, 1320, 1340, 1350, respectively. In addition, operation 1430 can apply to the second, or any subsequent group of CPR compressions.

Moreover, upon outputting the check patient prompt at operation 1450, it can be inquired according to an optional operation 1460 whether the impending and announced check pause will actually happen. For example, some timely confirmation may be expected by the user. If not received, then execution may revert to operation 1430.

As already mentioned, flowchart 1400 shows ways of performing embodiments in a continuous loop. For example, according to a subsequent operation 1480, the performing of the CPR compressions and, of course, their corresponding releases could be paused. This could be for performing a second check pause, a third check pause and so on. This pause would be from performing the CPR compressions and releases of the previous group, and may last for a pause time duration of at least 5 sec.

In addition, shortly before operation 1480, according to an optional operation 1478, a stopping count-down may be output. The stopping count-down may be synchronized with a beginning of the next check pause, i.e. of the pausing of the chest compressions of operation 1480. In some embodiments, the stopping count-down of operation 1478 is separate from the output prompt of operation 1450, for example as seen in flowchart 1400. In other embodiments the stopping count-down is part of the output prompt, as discussed above.

According to another operation 1490, a next group of the CPR compressions may restart being performed automatically, upon an end of the previous check pause. This next group may be the second group, the third, group, etc., and continue to be performed as per next operation 1430. In addition, shortly before operation 1490, according to another optional operation 1488, a human-perceptible restart warning may be output to the rescuer. The restart warning can be output in conjunction with the end of the check pause, and can be about the end of the check pause. As seen above, the restart warning may include a restart count-down synchronized with the end of the check pause.

Again, as mentioned above, the check pause of operation 1480 can be performed automatically, in connection with the check patient prompt being output, and without waiting for the rescuer to confirm it. The check pause can last for a pause time duration that can be updated, as per the above. Alternately, the user interface may further include a pause means that is configured to generate a pause input by the rescuer actuating it, which the rescuer would do upon the rescuer perceiving the check patient prompt. Then the check pause of operation 1480 can be performed responsive to the generated pause input.

Embodiments are now described where the rescuer can temporarily pause the CPR compressions. This can be accomplished in a number of ways where a CPR system includes one or more pause means that can be actuated by a rescuer. While a rescuer can often stop the CPR machine from performing compressions, pausing instead of stopping the performance of the CPR compressions may make more certain that the CPR compressions will restart after some time, without the rescuer forgetting to restart them.

Figure 15:
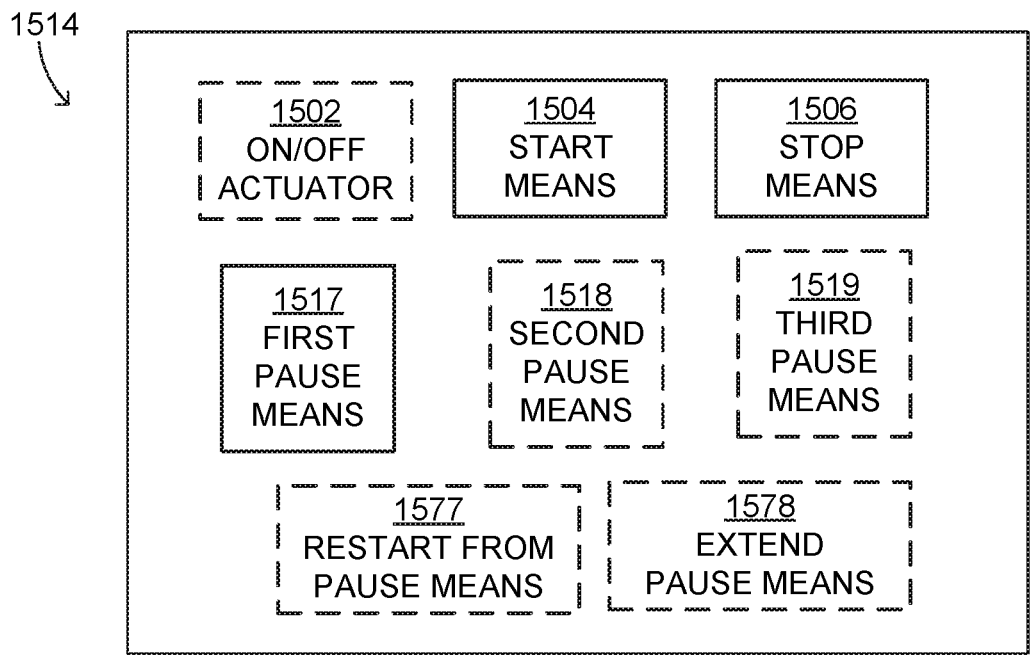
FIG. 15 is a block diagram of a sample user interface that includes various pause means, made according to embodiments.

FIG. 15 is a block diagram of a sample user interface (UI) 1514 that includes various pause means, made according to embodiments. UI 1514 optionally includes an ON/OFF actuator 1502, which may turn on and off the CPR machine. For example, when ON/OFF actuator 1502 is in the off position, a controller such as controller 410 may have no power, and so on.

User interface 1514 also includes a start means 1504. Start means 1504 can be configured to generate a start input responsive to being actuated by the rescuer. UI 1514 additionally includes a stop means 1506. Stop means 1506 can be configured to generate a stop input responsive to being actuated by the rescuer. UI 1514 further includes a pause means 1517, which can also be called a first pause means 1517. Pause means 1517 can be configured to generate a first pause input responsive to being actuated by the rescuer.

The start input, the stop input, and other inputs generated by the various pause means such as the first pause means can be internal to the CPR system. These internal inputs may be received by a processor such as processor 420, and accordingly control the compression mechanism. Controlling can be in various ways such that the CPR compressions are paused and restarted. Examples are now described.

Figure 16:
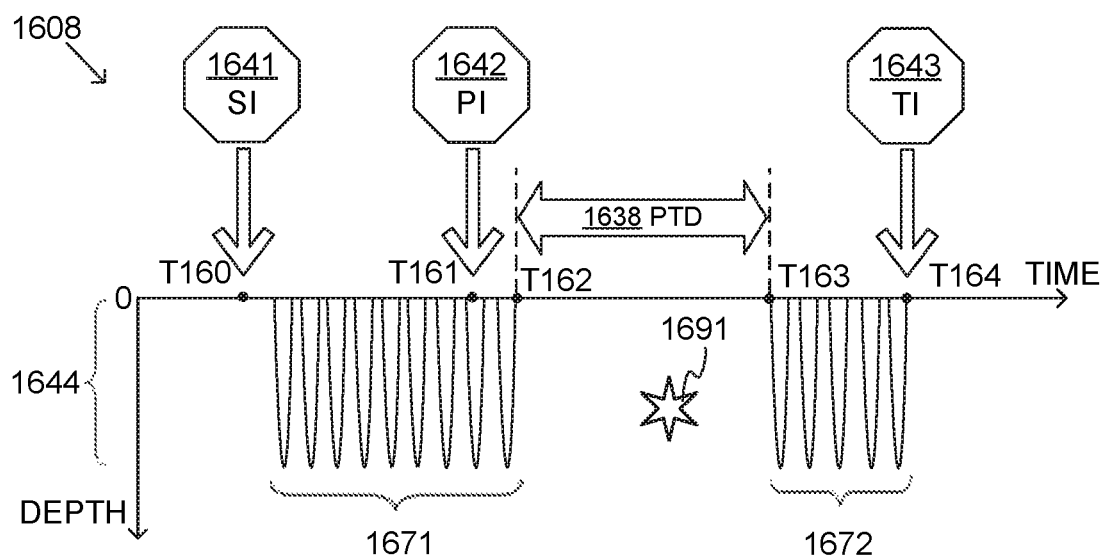
FIG. 16 is a time diagram of a sample sequence of CPR chest compressions that includes a pause responsive to a generated pause input, according to embodiments.

FIG. 16 is a time diagram of a sample sequence of CPR chest compressions that includes a pause due to a generated pause input, according to embodiments. In particular, FIG. 16 shows a time diagram 1608 of CPR chest compressions and releases 1644, which can be as described above. In addition, time diagram 1608 also shows a start input SI 1641, a pause input PI 1642, and a stop input TI 1643, such as were described above.

In time diagram 1608, the compression mechanism may start performing CPR compressions responsive to the generated start input SI 1641, which is received at time T160. Some of these compressions are shown as a first group 1671.

First pause input PI 1642 is generated at time T161. Then, responsive to the generated first pause input PI 1642, the compression mechanism may pause the performing of the CPR compressions. The pausing is indicated by a check pause 1691, which lasts between times T162 and T163. This duration is also known as pause time duration 1638. Pause time duration 1638 can be at least 5 sec long, as also described elsewhere in this document. During pause time duration 1638 the chest does not become compressed the same way as it was during the first group 1671 of CPR compressions. In fact, the chest might not become compressed at all. In fact, the compression mechanism may pause moving entirely.

The end of pause time duration PTD 1638 occurs at time T163. The compression mechanism may then automatically restart the performing of the CPR compressions, upon the end of pause time duration PTD 1638. This automatic restarting is part of the check pause 1691, and might not require any other intervention by the rescuer. Thus restarting the CPR compressions is shown by a second group 1672 of CPR compressions.

In time diagram 1608, stop input TI 1643 is generated at time T164. Responsive to the generated stop input TI 1643, compression mechanism may stop the performing of the CPR compressions.

Additional embodiments are now described.

Figure 17:
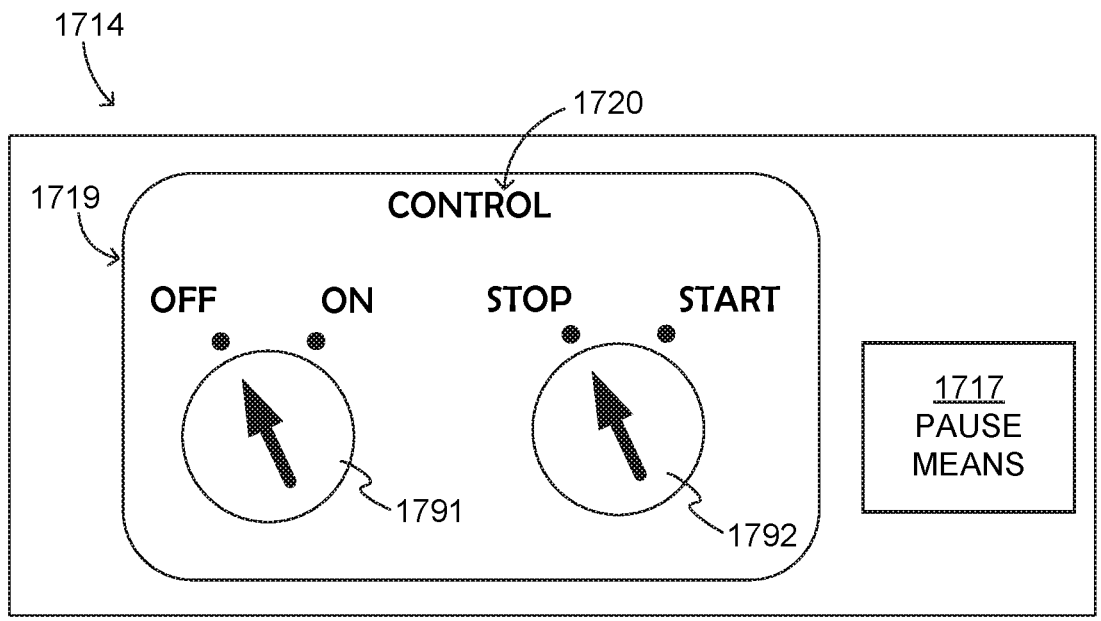
FIG. 17 is a diagram of a sample user interface showing particular embodiments for aspects of FIG. 15.

FIG. 17 is a diagram of a sample user interface (UI) 1714, showing particular embodiments for aspects of FIG. 15. A pause means 1717 is shown generically.

In addition, UI 1714 includes a section 1719 that has a label 1720. Label 1720 reads "CONTROL", and suggests control of the CPR machine portion of the CPR system.

In section 1719, an ON/OFF actuator 1791 is shown by a dial. Actuator 1791 can be configured to be actuated by the rescuer so that the ON/OFF actuator can be actuated to be in one of at least an ON state and an OFF state.

In section 1719, the start means and the stop means are implemented by a single start/stop actuator 1792 in the form of a dial 1792. Actuator 1792 can be configured to be actuated by the rescuer so that rotating the dial to the START label generates the start input, while rotating the dial back to the STOP label generates the stop input. Dial 1792 remains at the position it was rotated to last.

In some embodiments, the start means and the first pause means are implemented by a start/pause actuator. This can be implemented in a number of ways. An example is now described.

Figure 18:
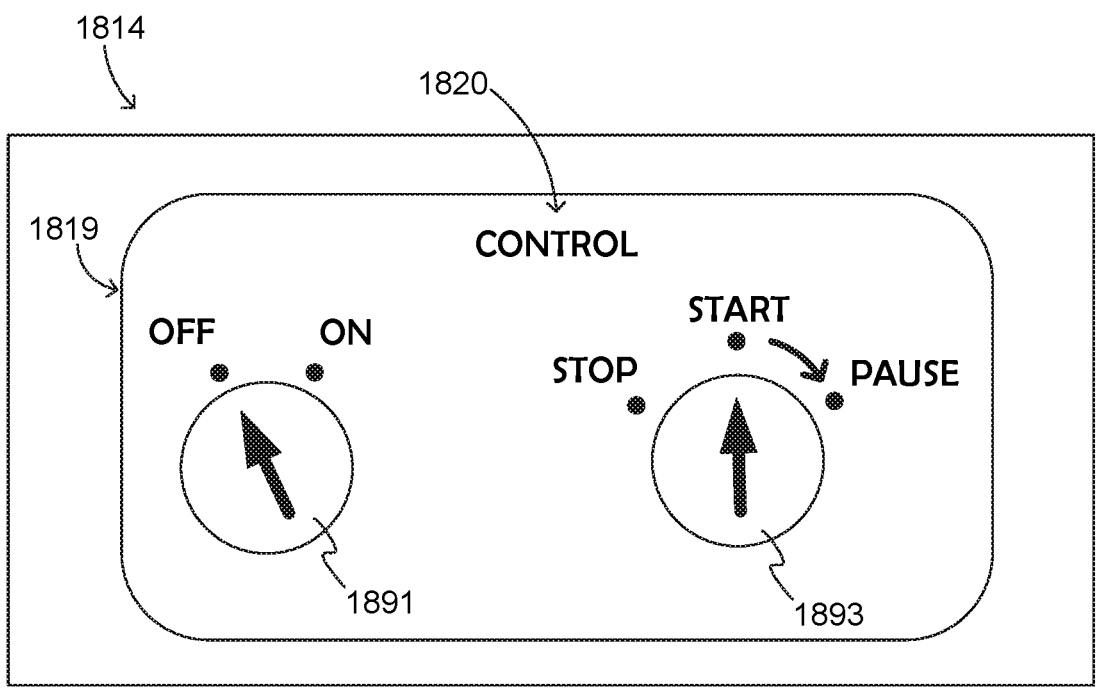
FIG. 18 is a diagram of a sample user interface showing a dial embodiment for a pause means of FIG. 17.

FIG. 18 is a diagram of a sample user interface 1814. UI 1814 includes a section 1819 that has a label 1820, similarly with FIG. 17. In section 1819, an ON/OFF actuator 1891 is similar to ON/OFF actuator 1791.

In section 1819, the start means, the stop means, and a pause means are implemented by a single special actuator 1893 in the form of a special dial 1893. Actuator 1893 works the same way as dial 1792, for generating the start and the stop inputs. In addition, rotating the dial from the START position to the PAUSE position generates the pause input; however, upon the rescuer releasing dial 1893 from the PAUSE position, dial 1893 returns automatically to the START position.

In some embodiments, the first pause means includes a button, which the rescuer can actuate by pressing. This can be implemented in a number of ways. Examples are now described, which apply for embodiments where the button is physical, or shown in a touchscreen of a device.

Figure 19:
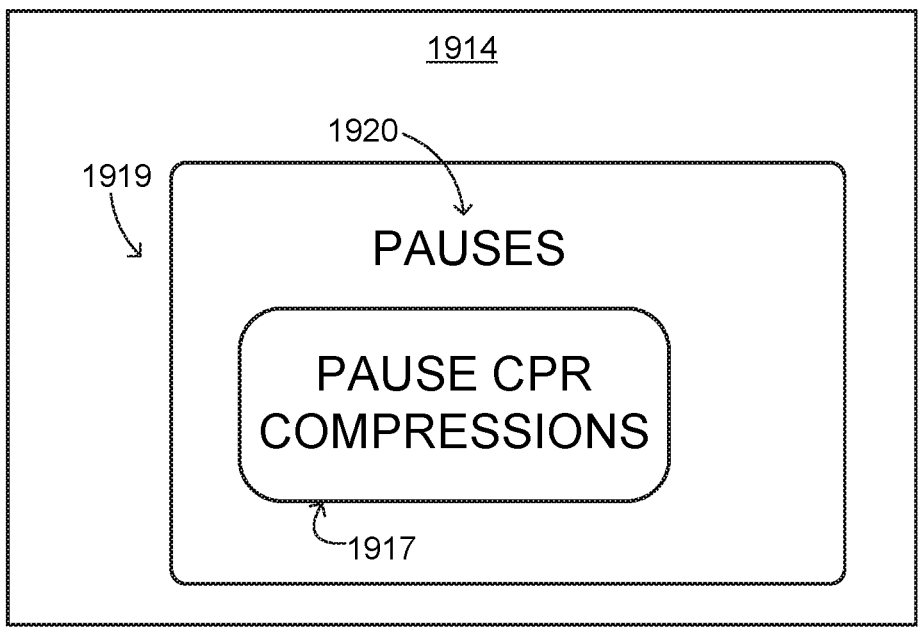
FIG. 19 is a diagram of a sample user interface showing a button embodiment for a pause means of FIG. 17.

FIG. 19 is a diagram of a sample user interface 1914. UI 1914 includes a section 1919 that has a label 1920. Label 1920 reads "PAUSES". Moreover, section 1919 includes a button 1917, which can be configured to generate a pause input responsive to being actuated by the rescuer.

A number of variations described elsewhere in this document may be combined with the pause means. For example, a human-perceptible indication can be output about the pausing of the performing of the CPR compressions, which can be a human-perceptible stopping count-down that is synchronized with a beginning of the pause time duration. In addition, time can be kept for the pause time duration. Plus, a value PTD 438 for the pause time duration can be stored in memory 430, and be updated as per the above. During the pause time duration, a specific point of a plunger of the compression mechanism can be automatically lifted by at least 3 cm from a reference elevation of the compressions. And, in conjunction with automatic restarting at the end of the pause time duration, a human-perceptible restart warning can be output to the rescuer. That restart warning may include a restart count-down that is synchronized with the end of the pause time duration, and so on.

In some embodiments, the user interface can have more than one pause means, for diverse functions about pausing. Examples are now described.

Embodiments can have different pause means, for causing a pause to have different scheduled pause time durations. For instance, returning to FIG. 15, user interface 1514 has a first pause means 1517, a second pause means 1518, and a third pause means 1519. In addition, UI 1514 has a restart from pause means 1577 and an extend pause means 1578. All these pause means, alone or in combination, can be implemented by actuators that can be actuated by the rescuer.

Figure 20:
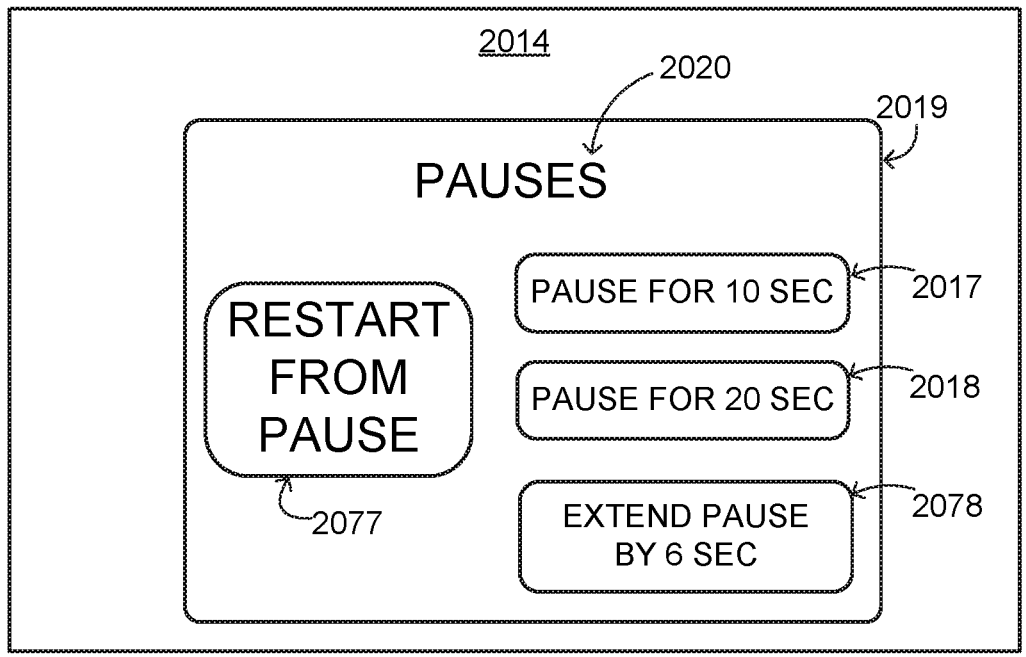
FIG. 20 is a diagram of a sample user interface showing sample button embodiments for aspects of FIG. 15.

FIG. 20 shows a button implementation of some of the pause means of FIG. 15. In particular, FIG. 20 shows a sample user interface (UI) 2014. UI 2014 includes a section 2019 that has a label 2020, similar to label 1920.

In section 2019, there is a first pause button 2017 and a second pause button 2018, which embody first pause means 1517 and second pause means 1518 respectively. These generate a first pause input and a second pause input, responsive to being actuated by the rescuer while the CPR compressions are being performed. Responsive to the generated second pause input, the performing of the CPR compressions becomes paused for an other pause time duration, and then may become automatically restarted after an end of the other pause time duration. The other pause time duration lasts at least 30% longer than the pause time duration. In the example of FIG. 20, the pause durations are written on pause buttons 2017, 2018. The pause time duration from button 2017 is 10 sec, and the pause time duration from button 2018 is 20 sec, i.e. it lasts 100% longer than the pause time duration from button 2017.

In the example of FIG. 20, buttons 2017 and button 2018 are labeled with the interval duration. The rescuer may push them as appropriate. For example, a 10-second pause may be deemed adequate for a pulse check, and a pause of 20 seconds may be deemed adequate for an intubation attempt on a patient with a difficult airway.

Alternately or in addition, such buttons could be labeled with the procedure for which they are deemed acceptable (e.g. "pulse check pause"). The rationale is that unacceptably long pauses will be avoided by having pauses that automatically end at acceptable durations.

In some embodiments, the rescuer may check the patient substantially faster than the scheduled pause time duration permits. In such embodiments, the rescuer may be enabled to restart the compressions faster than would happen according to the scheduled pause time duration. Examples are now described.

As seen previously in FIG. 15, UI 1514 has a restart from pause means 1577. Restart from pause means 1577 can be configured to generate a restart input, responsive to being actuated by the rescuer during the pause time duration but before the end of the pause time duration. In such embodiments, the performing of the CPR compressions is thus automatically restarted responsive to the restart input being generated, instead of upon the end of the pause time duration. In some embodiments, restart from pause means 1577 is distinct from the first pause means, for example as seen in button 2077 in FIG. 20.

Accordingly, actuating restart from pause means 1577 can end the pause faster than the scheduled time. As such, the pause can have an actual time duration that is less than the pause time duration that would be scheduled by the CPR system via value PTD 438. An example of this is now described.

Figure 21:
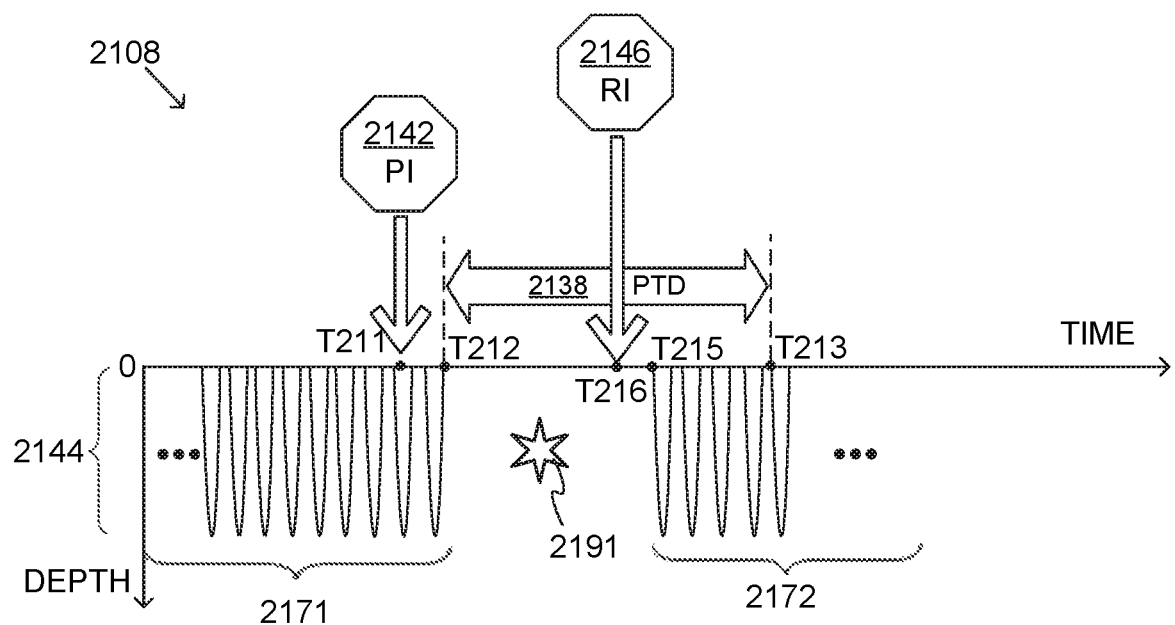
FIG. 21 is a time diagram of a sample of sequence of CPR chest compressions that includes a pause scheduled to last for a pause time duration, but whose actual time duration is shortened due to a generated restart from pause input, according to embodiments.

FIG. 21 is a time diagram 2108 of a sample sequence of CPR chest compressions and releases 2144. While a first group 2171 of CPR chest compressions is being performed, a pause input PI 2142 is generated at time T211. As a result, the CPR chest compressions are paused at time T212. A pause 2191 starts, which is scheduled to have a pause time duration PTD 2138. In other words, pause 2191 is scheduled to end at time T213. Of course, pauses like pause 2191 can also be thought of as check pauses.

During pause 2191, and at time T216, a restart input RI 2146 is generated, as described above. Responsive to restart input RI 2146, the CPR compressions restart at time T215 as a second group 2172. Time T215 is earlier than the scheduled time T213, and the actual time duration of pause 2191 was between T212 and T215.

In some embodiments, the CPR system can further be a learning system as to the actual pause time durations. For example, processor 420 can be configured to adjust stored value PTD 438 for the pause time duration, based upon when the restart input was generated, and thus based on the actual duration of pause 2191. Of course, in such embodiments where the adjustment happens during an event, it is preferred that the rescuer is aware that such adjustments could be taking place, that such automatic adjustments can be disabled, and so on.

In some embodiments, the rescuer may need more time to check the patient than the scheduled pause time duration permits. In such embodiments, the rescuer may be enabled to extend the pause for a longer time than the scheduled pause time duration. Examples are now described.

As seen previously in FIG. 15, UI 1514 has an extend pause means 1578. Extend pause means 1578 can be configured to generate an extend pause input, responsive to being actuated by the rescuer while the performing of the CPR compressions is thus paused. In such embodiments, the performing of the CPR compressions can be automatically thus restarted at least 4 sec later than the end of the pause time duration, instead of upon the end of the pause time duration, responsive to the generated extend pause input. This can be because, responsive to the generated extend pause input, the pause may be extended by an extended pause time duration.

Extend pause means 1578 can be implemented in different ways. In some embodiments, extend pause means 1578 is distinct from the first pause means, for example as seen in button 2078 in FIG. 20. In some embodiments, extend pause means 1578 is the same as the first pause means—for instance extend pause means 1578 could be implemented by button 1917 during the pause, in order to extend its duration from what would be scheduled.

Accordingly, the pause can have an actual time duration that is longer than the pause time duration that would be scheduled by the CPR system via value PTD 438. An example of this is now described.

Figure 22:
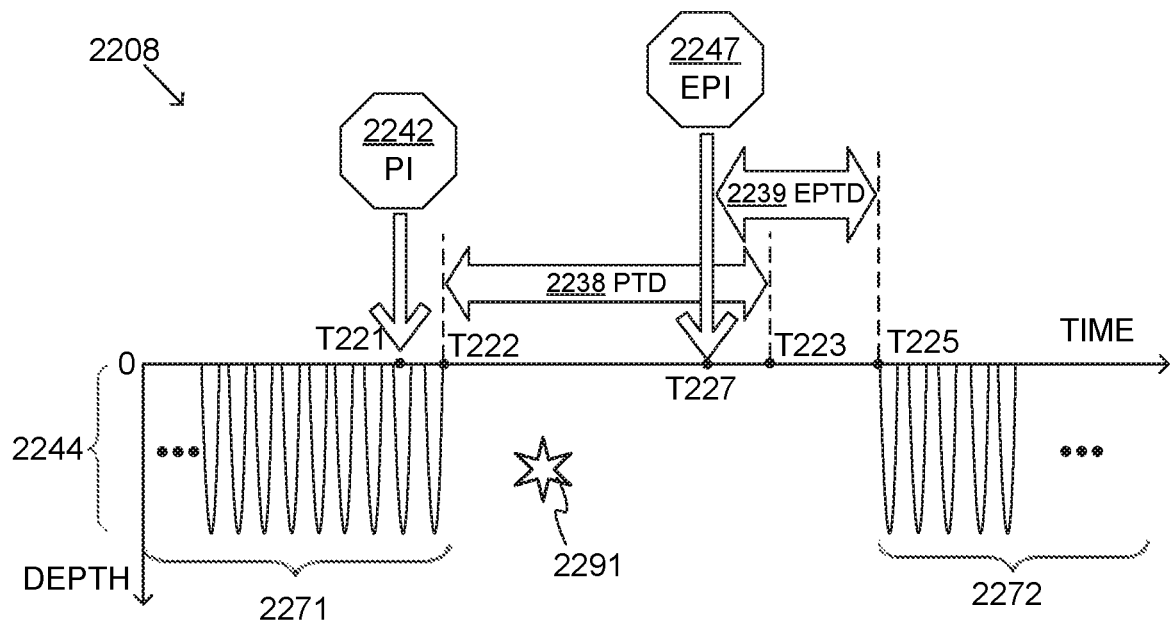
FIG. 22 is a time diagram of a sample of sequence of CPR chest compressions that includes a pause scheduled to last for a pause time duration, but whose actual time duration is extended due to a generated extend pause input, according to embodiments.

FIG. 22 is a time diagram 2208 of a sample sequence of CPR chest compressions and releases 2244. While a first group 2271 of CPR chest compressions is being performed, a pause input PI 2242 is generated at time T221. As a result, the CPR chest compressions are paused at time T222. A pause 2291 starts, which is scheduled to have a pause time duration PTD 2238. In other words, pause 2291 is scheduled to end at time T223.

During pause 2291, and at time T227, an extend pause input EPI 2247 is generated, as described above. Responsive to extend pause input EPI 2247, pause 2291 can become prolonged by an extended pause time duration EPTD 2239. As such, the CPR compressions may restart at time T225 as a second group 2272. Time T225 is later than the scheduled time T223, and the actual time duration of pause 2291 was between T222 and T225. And, of course, the rescuer can cause another extend pause input to be generated to further extend the pause, and so on.

And, in learning system embodiments, processor 420 can be configured to adjust stored value PTD 438 for the pause time duration, based upon when the extend pause input was generated, and thus based on the actual duration of pause 2291.

Figure 23:
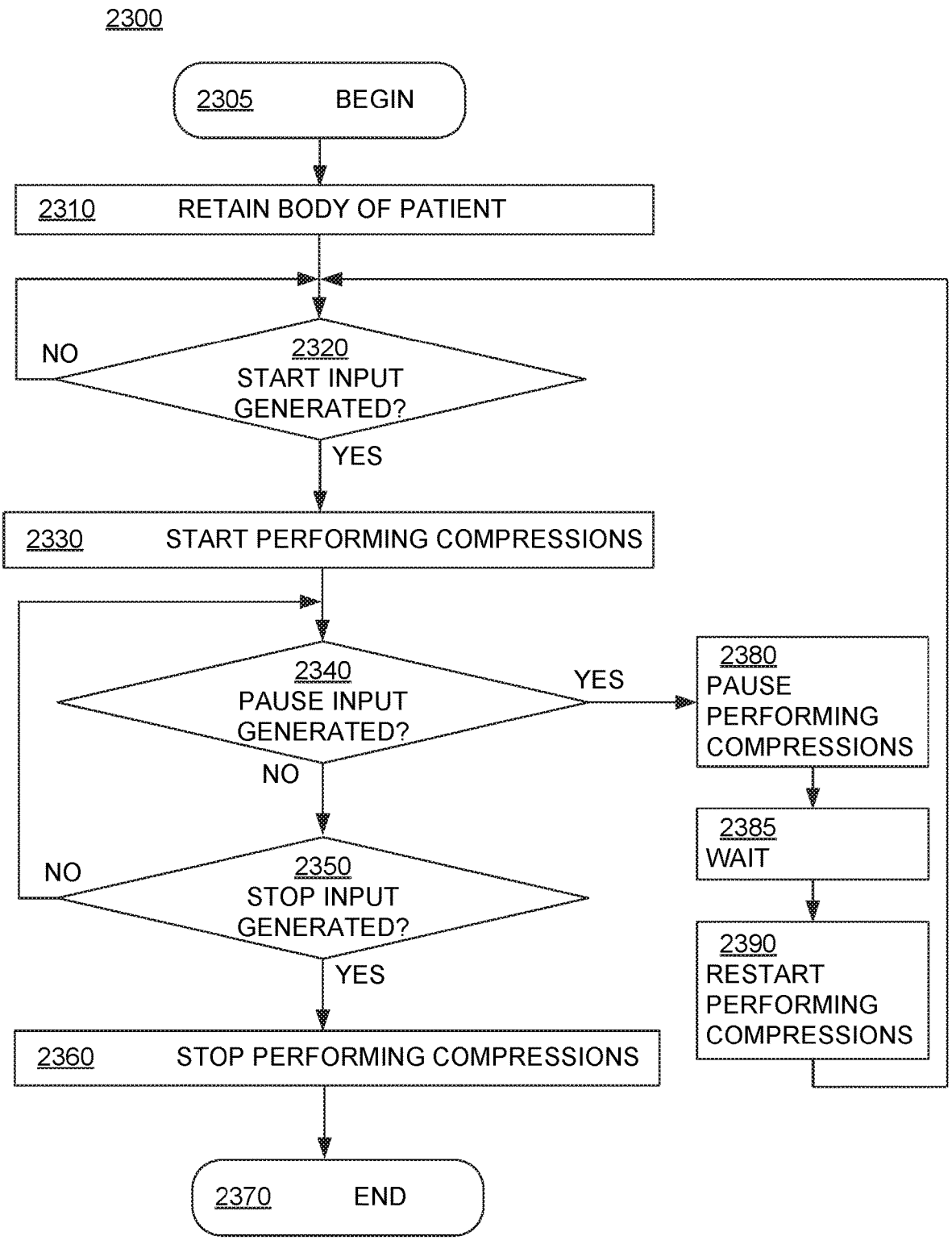
FIG. 23 is a flowchart for illustrating methods according to embodiments.

FIG. 23 shows a flowchart 2300 for describing methods according to embodiments. Such methods may be implemented by a CPR system that includes a retention structure, a compression mechanism attached to the retention structure, and a user interface that has a start means, a stop means, and a first pause means.

Execution may begin at a step 2305. According to a next operation 2310, a body of a patient may be retained by the retention structure.

According to an other operation 2320, it can be determined whether a start input was generated, responsive to the start means being actuated by the rescuer. While the answer is no, execution may return to operation 2320.

If at operation 2320 the answer becomes yes then, according to another operation 2330, CPR compressions and releases may start to be performed by the compression mechanism to a chest of the body while the body is thus retained. This would happen responsive to the start input generated at operation 2320.

According to another operation 2340, it can be determined whether a first pause input generated, responsive to the first pause means being actuated by the rescuer. While the answer is no then, according to another operation 2350, it can be determined whether a stop means was generated, responsive to the stop means being actuated by the rescuer.

While the answer in operation 2350 is no, then execution may proceed to operation 2340. If the answer at operation 2350 becomes yes then, according to another operation 2360, the performing the CPR compressions may be stopped, responsive to the stop input generated at operation 2350. Then execution may end at a next step 2370.

If the answer at operation 2340 becomes yes then, according to another operation 2380, the performing of the CPR compressions may be paused, responsive to the first pause input generated at operation 2340.

Then, according to another operation 2385, the CPR compression mechanism may wait. Waiting can be for a pause time duration, which can be shortened or extended as above. During operation 2385, the chest might not become compressed the way it started becoming compressed at operation 2330.

Then, according to another, operation 2390, the performing of the CPR compressions can be automatically restarted, upon an end of the pause time duration.

In the methods described above, each operation can be performed as an affirmative step of doing, or causing to happen, what is written that can take place. Such doing or causing to happen can be by the whole system or device, or just one or more components of it. It will be recognized that the methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily this description. Plus, any reference to any prior art in this description is not, and should not be taken as, an acknowledgement or any form of suggestion that such prior art forms parts of the common general knowledge in any country or any art.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to" and/or "configured to" denote one or more actual states of construction and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

In this description a single reference numeral may be used consistently to denote a single item, aspect, component, or process. Moreover, a further effort may have been made in the drafting of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

This disclosure, which may be referenced elsewhere as "3462", is meant to be illustrative and not limiting on the scope of the following claims. The claims of this document define certain combinations and subcombinations of elements, features and steps or operations, which are regarded as novel and non-obvious. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that it can have one or more of this component or item.

What is claimed:

1. A Cardio-Pulmonary Resuscitation (CPR) system, the CPR system comprising:
    a compression mechanism attached to a retention structure, the compression mechanism configured to perform CPR compressions to a chest of a patient alternating with releases of the CPR compressions;
    a controller configured to:
        control the compression mechanism to perform a first group of the CPR compressions,
        stop performing lasting a predetermined amount of time during a first check pause,
        at the end of the first check pause, control the compression mechanism to perform a second group of the CPR compressions, and
        determine whether a check patient condition has been met based at least on a determination of whether a threshold number of the CPR compressions have been performed in the second group of the CPR compressions and whether a pause instruction has been received from another device, the check patient condition being met when either or both of the threshold number of the CPR compressions being performed and the pause instruction being received from the other device are satisfied, and
        when the check patient condition is met, stop performing the second group of the CPR compressions for a second check pause lasting the predetermined amount of time; and
    a user interface configured to output a human-perceptible check patient prompt responsive when the check patient condition is met, the check patient prompt reminding a rescuer to check the patient for a non-ventilation condition.

2. The CPR system of claim 1, in which
the compression mechanism includes a plunger, and
the controller is further configured to:
    during the performance of the first group of the CPR compressions, start one of the CPR compressions from a first elevation based on a specific point of the plunger, and
    during the first check pause, the specific point is automatically lifted by a predetermined distance from the first elevation.

3. The CPR system of claim 1, further comprising:
    a counter initialized to count a number of the CPR compressions in the second group, and
    in which a number of the CPR compressions in the second group are counted by the counter, and
    the check patient condition is met when the counted number reaches the threshold number.

4. The CPR system of claim 3, in which the counter becomes re-initialized to count a number of the CPR compressions in a subsequent group when the second check pause in the CPR compressions has lasted at least 3 seconds.

5. The CPR system of claim 1, further comprising:
    a time keeping mechanism, and
    in which time is kept by the time keeping mechanism for the second group of the CPR compressions, and
    the check patient condition is met when the kept time exceeds a check time duration, the check time duration lasting at least 1.5 minutes.

6. The CPR system of claim 5, in which the time keeping mechanism becomes re-initialized when the second check pause has lasted at least 3 seconds.

7. The CPR system of claim 5, further comprising:
    a memory configured to store a value for the check time duration; and
    a communication module configured to receive a remote check time duration input, and
    in which the stored value for the check time duration becomes adjusted responsive to the received remote check time duration input.

8. The CPR system of claim 5, further comprising:
a memory configured to store a value for the check time duration, and
in which the user interface is further configured to receive a local check time duration input, and
the stored value for the check time duration becomes adjusted responsive to the received local check time duration input.

9. The CPR system of claim 1, in which the user interface is physically coupled to the retention structure.

10. A Cardio-Pulmonary Resuscitation (CPR) system, the CPR system comprising:
a retention structure configured to retain a body of a patient;
a communication module configured to receive a pause instruction from another device;
a compression mechanism attached to the retention structure, the compression mechanism configured to perform CPR compressions to a chest of the patient alternating with releases of the CPR compressions;
a controller configured to:
control the compression mechanism to perform a first group of the CPR compressions,
stop performing AMD b3 during a first check pause lasting a predetermined amount of time,
at the end of the first check pause, control the compression mechanism to perform a second group of the CPR compressions,
determine whether a check patient condition is met based at least on a determination of whether a threshold number of the CPR compressions have been performed in the second group of the CPR compressions and whether the pause instruction has been received from the other device, the check patient condition being met when either or both of the threshold number of the CPR compressions being performed and the pause instruction being received from the other device are satisfied, and
when the check patient condition is met, stop performing AMD b4 for a second check pause lasting the predetermined amount of time; and
a user interface configured to output a human-perceptible check patient prompt responsive when the check patient condition is met, the check patient prompt reminding a rescuer to check the patient for a non-ventilation condition.

11. The CPR system of claim 10, further comprising:
a parameter sensor configured to detect a parameter about the patient, and to output a parameter sensor signal indicative of a dynamic value of the parameter, and
in which the check patient condition further includes that a stoppage criterion is met by the dynamic value, even if the threshold number of the CPR compressions in the second group has not been performed yet.

12. The CPR system of claim 11, in which the parameter is detected while the second group of the CPR compressions is being performed.

13. The CPR system of claim 11, in which the check patient condition includes that the stoppage criterion is met by the dynamic value after the second group of the CPR compressions has been performed uninterrupted for at least one minute.

14. The CPR system of claim 11, in which the retention structure includes a strap configured to be used by the rescuer to restrain a motion of the patient's body, and a force sensor configured to detect a change in the force applied to the strap, and the stoppage criterion is met when a detected change in the force applied to the strap reaches a threshold.

15. The CPR system of claim 10, in which
the compression mechanism includes a plunger, and
the controller is further configured to:
during the performance of the first group of the CPR compressions, start one of the CPR compressions from a first elevation based on a specific point of the plunger, and
during the check pause, the specific point is automatically lifted by a predetermined distance from the first elevation.

16. The CPR system of claim 10, further comprising:
a force sensor configured to detect a force/motion relationship of the CPR compressions, and to output a force signal indicative of a dynamic value of the force/motion relationship, and
in which the check patient condition includes that a change in the detected force/motion relationship is above a threshold, even if the threshold number of the CPR compressions in the second group has not been performed yet.

17. The CPR system of claim 10, further comprising:
a counter initialized to count a number of the CPR compressions in the second group, and
in which the number of the CPR compressions in the second group are counted by the counter, and
the check patient condition is met when the counted number reaches the threshold number.

18. The CPR system of claim 17, in which the counter becomes re-initialized to count a number of the CPR compressions in a subsequent group of compressions after the second check pause has lasted the predetermined amount of time.

* * * * *

UNITED STATES PATENT AND TRADEMARK OFFICE
CERTIFICATE OF CORRECTION

| | |
|---|---|
| PATENT NO. | : 12,239,600 B2 |
| APPLICATION NO. | : 17/026701 |
| DATED | : March 4, 2025 |
| INVENTOR(S) | : Erik von Schenck et al. |

It is certified that error appears in the above-identified patent and that said Letters Patent is hereby corrected as shown below:

In the Claims

In Claim 10, at Column 27, Line 24:
"AMD b3"
Should read:
--the first group of the CPR compressions--.

In Claim 10, at Column 27, Line 40:
"AMD b4"
Should read:
--the second group of the CPR compressions--.

Signed and Sealed this
Fifteenth Day of April, 2025

Coke Morgan Stewart
*Acting Director of the United States Patent and Trademark Office*